(12) United States Patent
Hui

(10) Patent No.: US 7,700,318 B2
(45) Date of Patent: Apr. 20, 2010

(54) CHIMERIC POLYPEPTIDE AND USE THEREOF

(75) Inventor: Mizhou Hui, Thousand Oaks, CA (US)

(73) Assignee: Amprotein Corporation, Camarillo, CA (US)

( * ) Notice: Subject to any disclaimer, the term of this patent is extended or adjusted under 35 U.S.C. 154(b) by 864 days.

(21) Appl. No.: 10/576,995

(22) PCT Filed: Aug. 25, 2004

(86) PCT No.: PCT/US2004/027655

§ 371 (c)(1), (2), (4) Date: Oct. 4, 2006

(87) PCT Pub. No.: WO2005/021578

PCT Pub. Date: Mar. 10, 2005

(65) Prior Publication Data

US 2007/0082379 A1     Apr. 12, 2007

Related U.S. Application Data

(60) Provisional application No. 60/497,988, filed on Aug. 26, 2003.

(51) Int. Cl.
*C12P 21/06* (2006.01)
*C12N 1/20* (2006.01)
*C12N 15/00* (2006.01)
*C12N 5/00* (2006.01)
*C12N 5/02* (2006.01)
*C12N 15/74* (2006.01)
*C07K 1/00* (2006.01)
*C07K 14/00* (2006.01)
*C07K 16/00* (2006.01)
*C07K 17/00* (2006.01)
*C08H 1/00* (2006.01)
*A61K 38/00* (2006.01)

(52) U.S. Cl. ............ 435/69.1; 435/252.3; 435/320.1; 435/325; 435/471; 530/350; 530/402; 514/12

(58) Field of Classification Search ............... None
See application file for complete search history.

(56) References Cited

U.S. PATENT DOCUMENTS 6,294,170 B1    9/2001  Boone et al.
6,617,135 B1 *  9/2003  Gillies et al. ............ 435/69.7
2006/0275868 A1 * 12/2006  Smith ........................ 435/69.1

FOREIGN PATENT DOCUMENTS

WO    WO03/010202    2/2003

OTHER PUBLICATIONS

Kim et al., "Ex Vivo Gene Delivery of IL-1 Ra and Soluble TNF Receptor Confers a Distal Synergistic Therapeutic Effect in Antigen-Induced Arthritis," Molecular Therapy, vol. 6, No. 5, pp. 591-600 (2002).
Ghivizzani et al., "Direct Adenovirus-Mediated Gene Transfer of Interleukin 1 and Tumor Necrosis Factor α Soluble Receptors to Rabbit Knees with Experimental Arthritis has Local and Distal Anti-Arthritic Effects," *Proc. Natl. Acad. Sci. USA*, vol. 95, pp. 4613-4618 (1998).

* cited by examiner

*Primary Examiner*—Robert Landsman
(74) *Attorney, Agent, or Firm*—Occhiuti Rohlicek & Tsao LLP

(57) ABSTRACT

A chimeric polypeptide comprising a TNF neutralizer domain, an IL-1 receptor antagonist domain, and a dimerization domain, wherein the three domains are operably linked to each other. Within the scope of this invention are (i) nucleic acids encoding the polypeptide; (ii) expression vectors and host cells containing the nucleic acids; (iii) related pharmaceutical compositions; and (iii) related preparation and treatment methods.

23 Claims, 9 Drawing Sheets

Figure 1: 1st generation of production clones of TNFRII-Fc and TNFRII-Fc-IL1ra chimera: 24-well plate expression in serum-free medium TNFRII-Fc-IL-1ra chimera In-house TNFRII-Fc TNFRII-Fc marketed Albumin Direct CM protein Coomasie blue staining to visualize the protein products

Figure 2: Affinity purification of chimeric TNFRII-Fc-Il-1ra

Non-reduced

Reduced

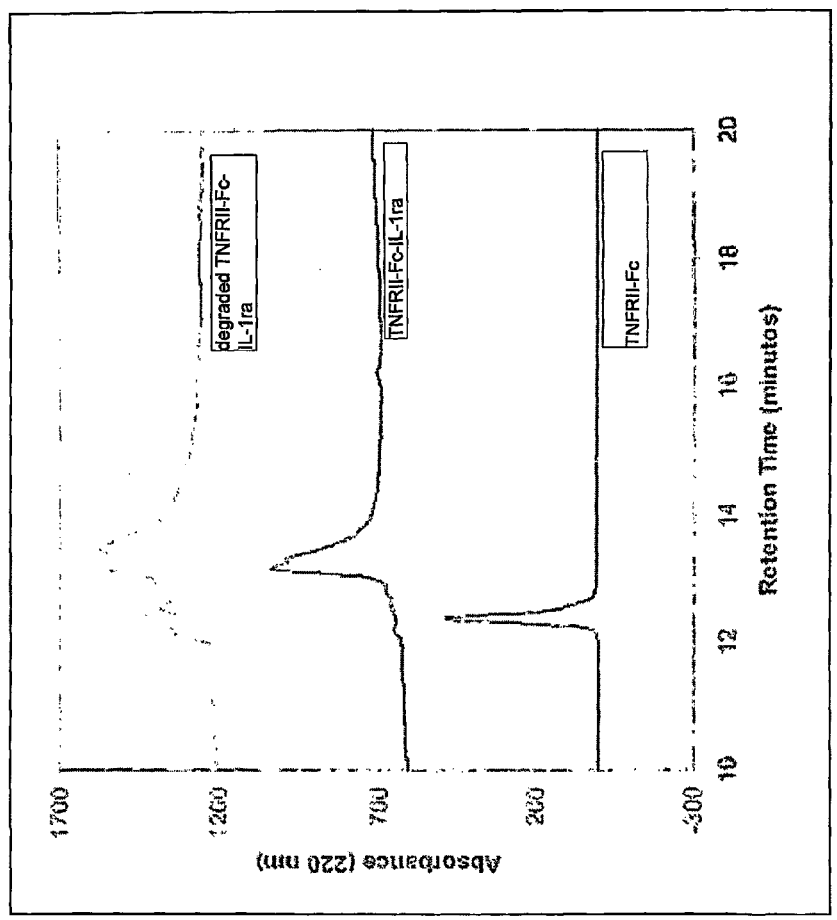
Figure 3: An example of our troubleshooting capability: reducing a degradation problem for chimeric TNFRII-Fc-IL-1ra by altering the first purification step: HPLC analysis of intact and partially degraded chimeric TNFRII-Fc-IL-1ra with TNFRII-Fc control.

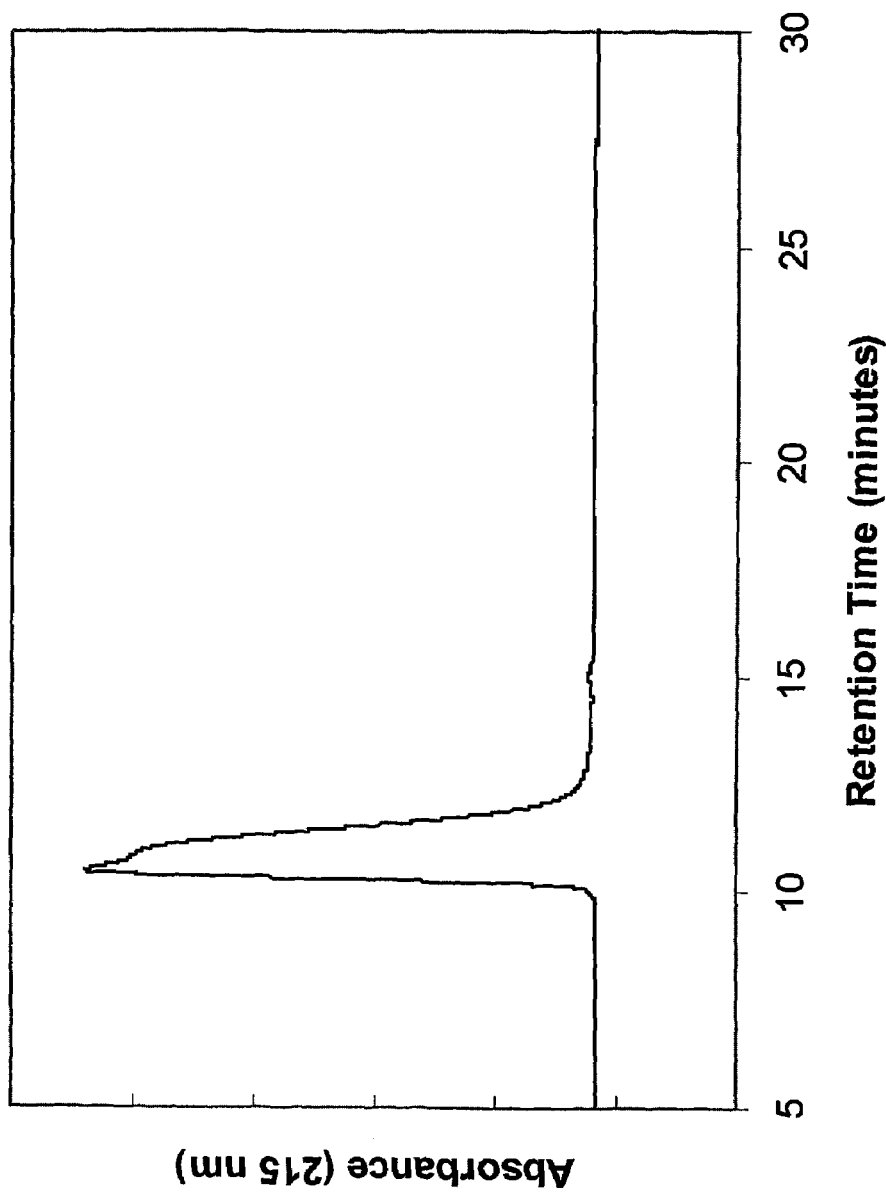
Figure 4: SEC-HPLC analysis of TNFRII-Fc-IL-1ra after formulation and lyophilization

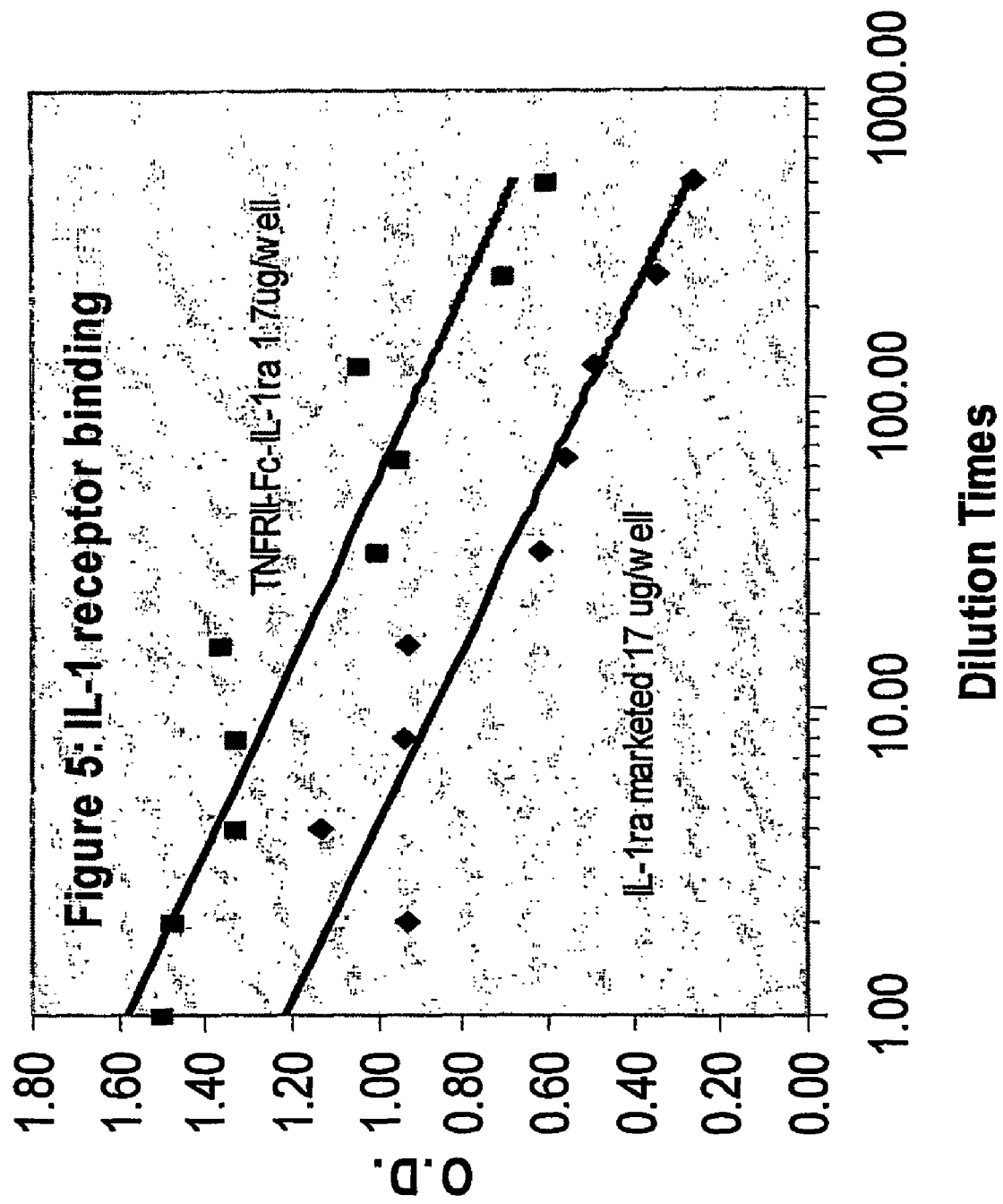

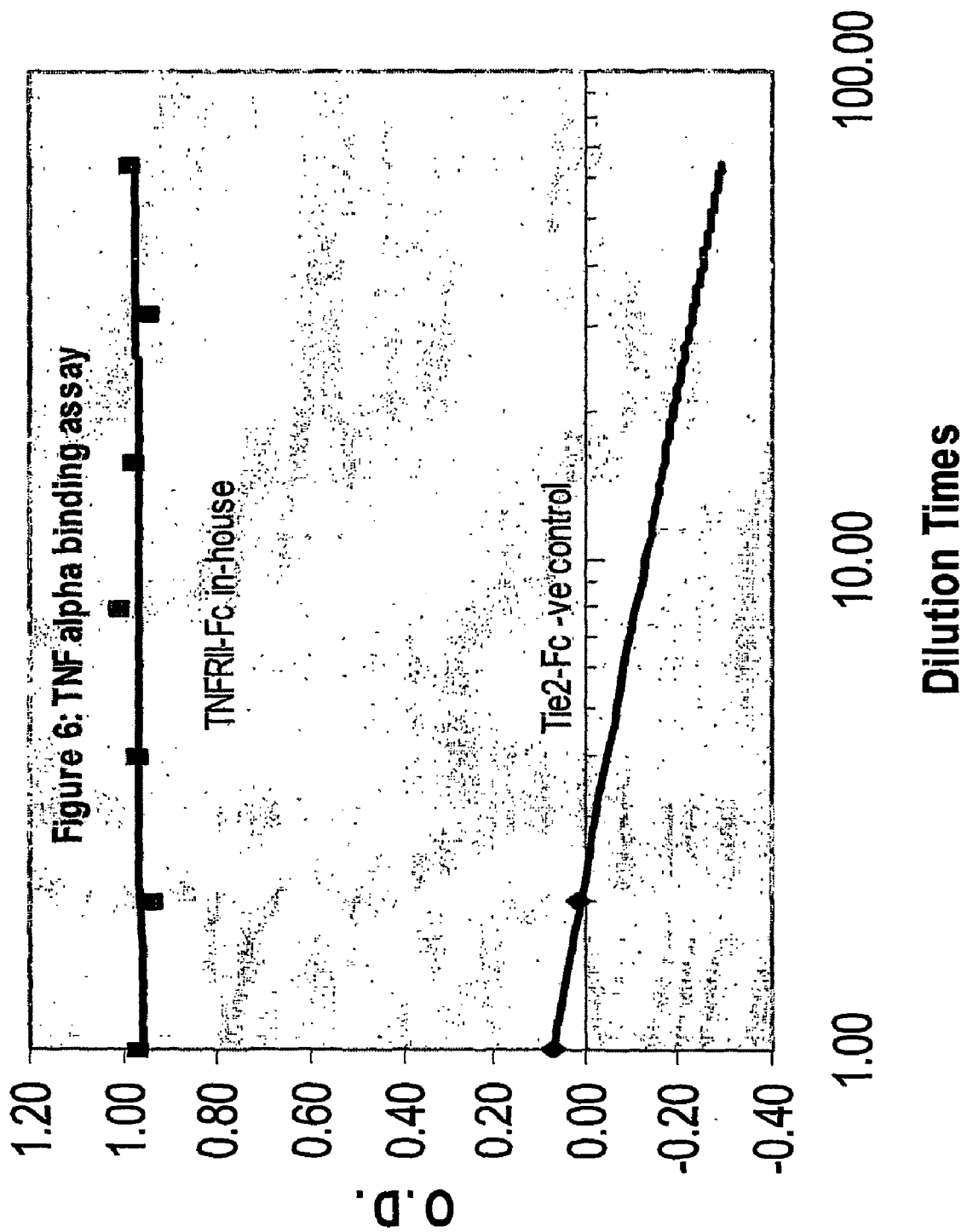

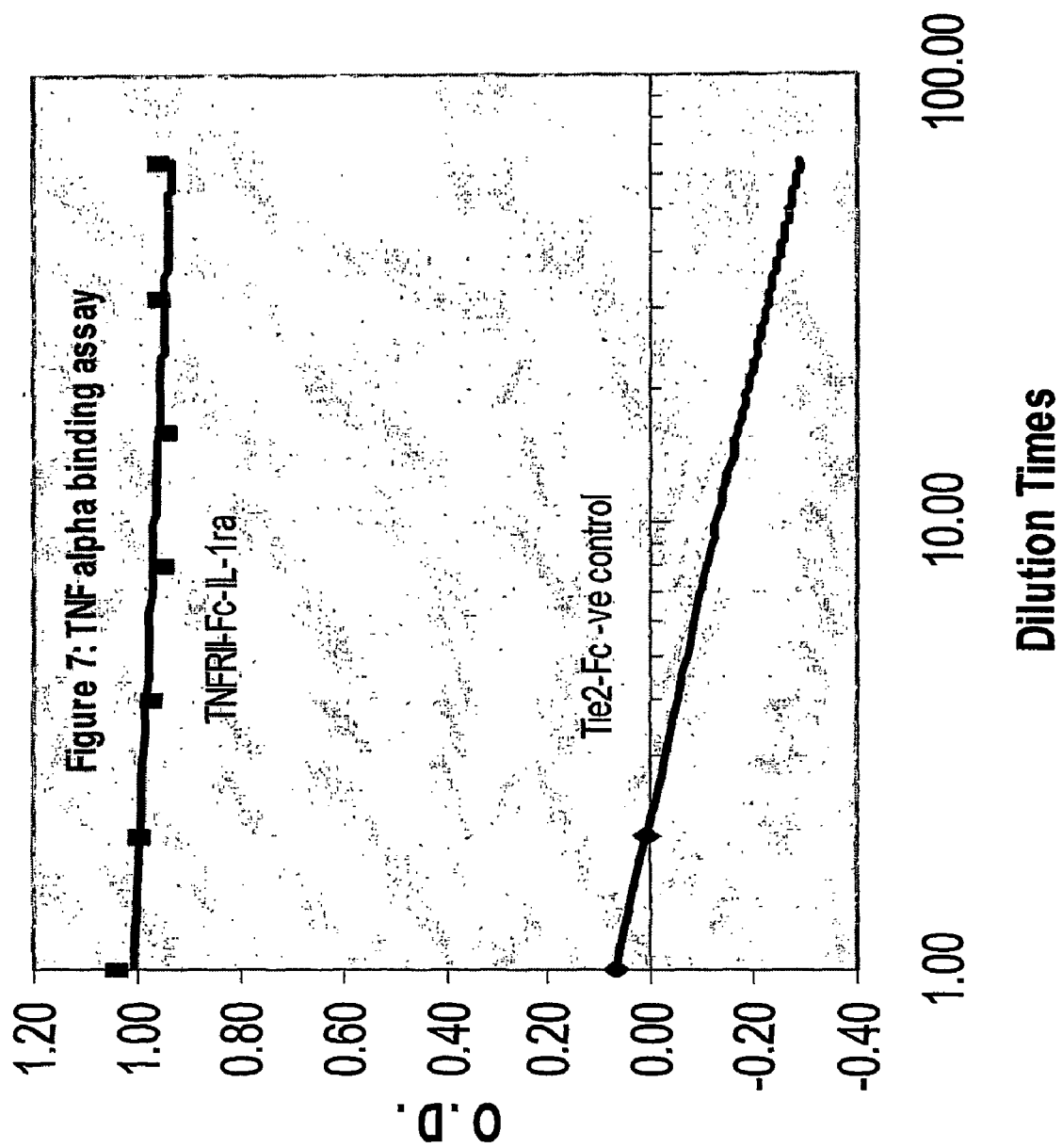

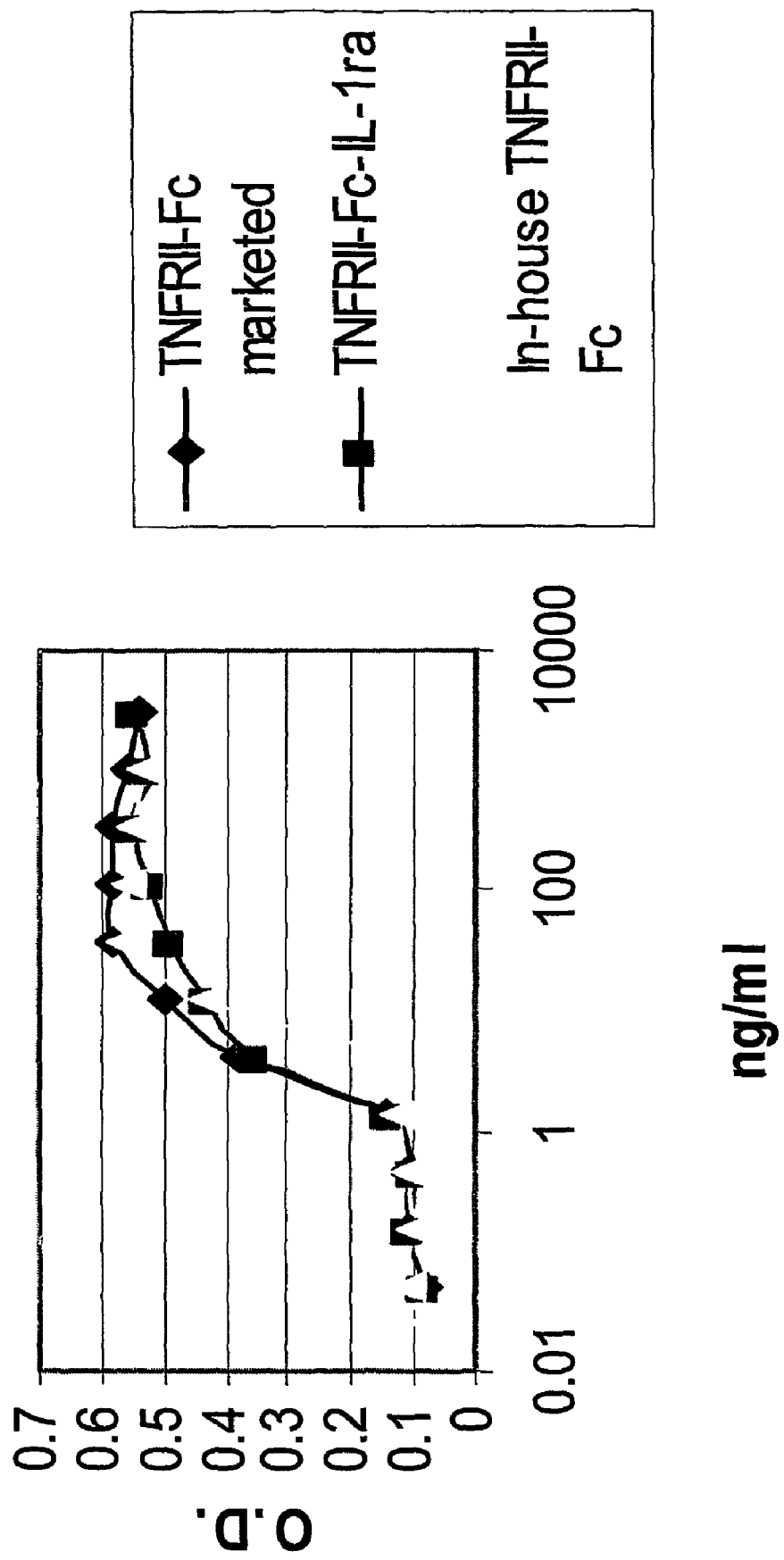
Figure 8: Cell-based TNF alpha neutralization test

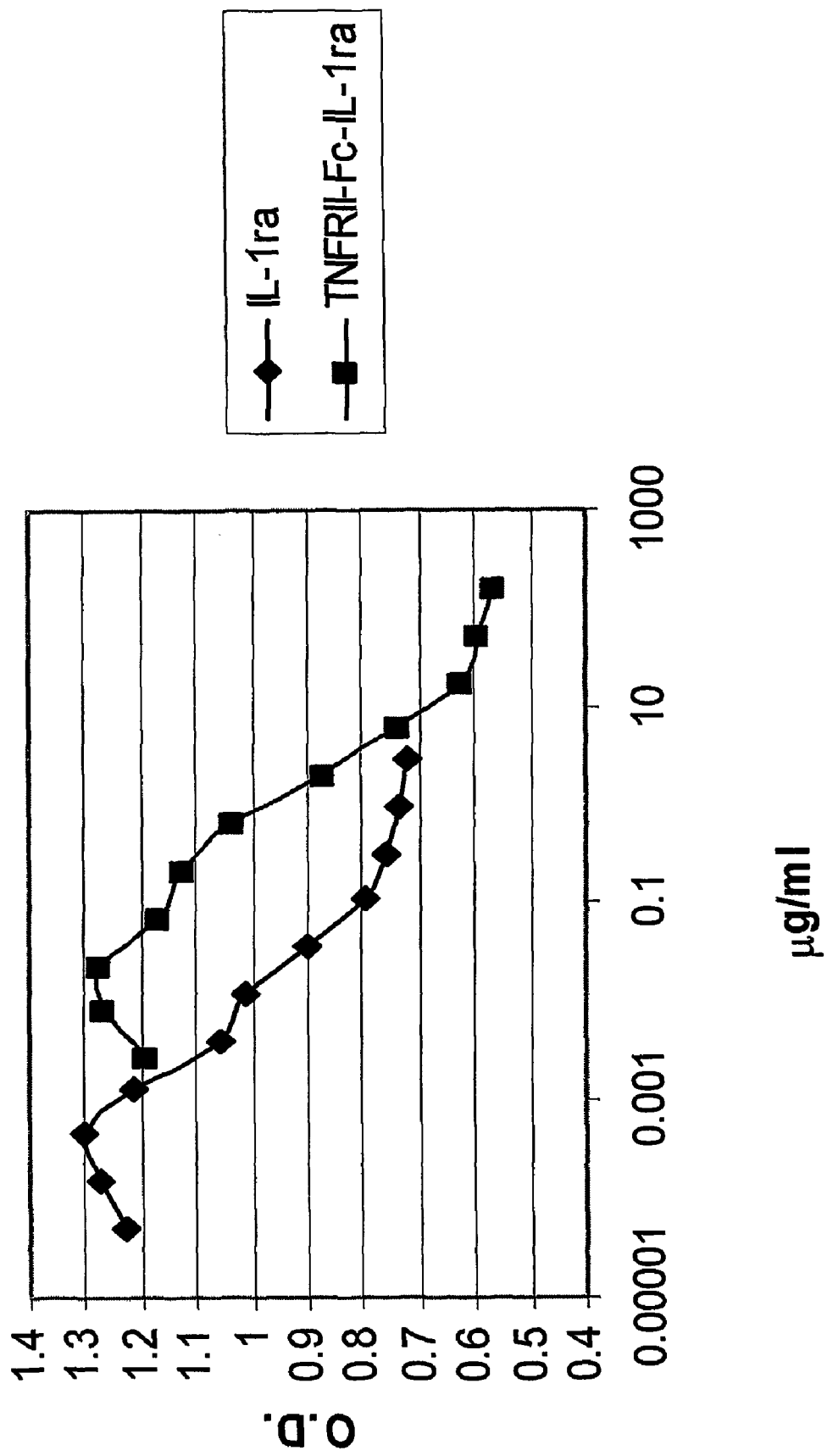

SEQUENCE LISTING

<160> NUMBER OF SEQ ID NOS: 8

<210> SEQ ID NO 1
<211> LENGTH: 1923
<212> TYPE: DNA
<213> ORGANISM: Artificial Sequence
<220> FEATURE:
<223> OTHER INFORMATION: Description of Artificial Sequence: Synthetic construct

<400> SEQUENCE: 1

```
atggcgcccg tcgccgtctg ggccgcgctg ccgtcggac tggagctctg ggctgcggcg      60
cacgccttgc ccgcccaggt ggcatttaca ccctacgccc cggagcccgg gagcacatgc     120
cggctcagag aatactatga ccagacagct cagatgtgct gcagcaaatg ctcgccgggc     180
caacatgcaa aagtcttctg taccaagacc tcggacaccg tgtgtgactc ctgtgaggac     240
agcacataca cccagctctg gaactgggtt cccgagtgct tgagctgtgg ctcccgctgt     300
agctctgacc aggtggaaac tcaagcctgc actcgggaac agaaccgcat ctgcacctgc     360
aggcccggct ggtactgcgc gctgagcaag caggagggg gccggctgtg cgcgccgctg     420
cgcaagtgcc gcccgggctt cggcgtggcc agaccaggaa ctgaaacatc agacgtggtg     480
tgcaagccct gtgccccggg gacgttctcc aacacgactt catccacgga tatttgcagg     540
ccccaccaga tctgtaacgt ggtggccatc cctgggaatg caagcatgga tgcagtctgc     600
acgtccacgt cccccacccg gagtatggcc caggggcag tacttacc ccagccagtg        660 tccacacgat cccaacacac gcagccaact ccagaaccca gcactgctcc aagcacctcc     720
ttcctgctcc aatgggccc cagcccccca gctgaaggga gcactggcga cgagcccaaa     780
tcttgtgaca aaactcacac atgcccaccg tgcccagcac ctgaactcct ggggggaccg     840
tcagtcttcc tcttccccc aaaacccaag gacaccctca tgatctcccg gacccctgag     900
gtcacatgcg tggtggtgga cgtgagccac gaagaccctg aggtcaagtt caactggtac     960
gtggacggcg tggaggtgca taatgccaag acaaagccgc gggaggagca gtacaacagc    1020
acgtaccgtg tggtcagcgt cctcaccgtc ctgcaccagg actggctgaa tggcaaggag    1080
tacaagtgca aggtctccaa caaagcctc ccagccccca tcgagaaaac catctccaaa     1140
gccaaagggc agccccgaga accacaggtg tacaccctgc ccccatcccg ggatgagctg    1200
accaagaacc aggtcagcct gacctgcctg gtcaaaggct tctatcccag cgacatcgcc    1260
gtggagtggg agagcaatgg gcagccggag aacaactaca agaccacgcc tcccgtgctg    1320
gactccgacg gctccttctt cctctacagc aagctcaccg tggacaagag caggtggcag    1380
caggggaacg tcttctcatg ctccgtgatg catgaggctc tgcacaacca ctacacgcag    1440
aagagcctct ccctgtctcc gggtaaacga ccctctggga gaaaatccag caagatgcaa    1500
gccttcagaa tctgggatgt taaccagaag accttctatc tgaggaacaa ccaactagtt    1560
gctggatact gcaaggacc aaatgtcaat ttaaaagaaa agatagatgt ggtacccatt      1620
gagcctcatg ctctgttctt gggaatccat ggagggaaga tgtgcctgtc ctgtgtcaag    1680
tctggtgatg agaccagact ccagctggag gcagttaaca tcactgacct gagcgagaac    1740
agaaagcagg acaagcgctt cgccttcatc cgctcagaca gtggcccac caccagtttt     1800 gagtctgccg cctgccccgg ttggttcctc tgcacagcga tggaagctga ccagcccgtc    1860
```
agcctcacca atatgcctga cgaaggcgtc atggtcacca aattctactt ccaggaggac    1920
gag                                                                  1923

<210> SEQ ID NO 2
<211> LENGTH: 619
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 2

Leu Pro Ala Gln Val Ala Phe Thr Pro Tyr Ala Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

-continued

```
Lys Glu Tyr Lys Cys Lys Val Ser Asn Lys Ala Leu Pro Ala Pro Ile
                340                 345                 350
Glu Lys Thr Ile Ser Lys Ala Lys Gly Gln Pro Arg Glu Pro Gln Val
            355                 360                 365
Tyr Thr Leu Pro Pro Ser Arg Asp Glu Leu Thr Lys Asn Gln Val Ser
        370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
450                 455                 460
Pro Gly Lys Arg Pro Ser Gly Arg Lys Ser Ser Lys Met Gln Ala Phe
465                 470                 475                 480
Arg Ile Trp Asp Val Asn Gln Lys Thr Phe Tyr Leu Arg Asn Asn Gln
                485                 490                 495
Leu Val Ala Gly Tyr Leu Gln Gly Pro Asn Val Asn Leu Lys Glu Lys
            500                 505                 510
Ile Asp Val Val Pro Ile Glu Pro His Ala Leu Phe Leu Gly Ile His
        515                 520                 525
Gly Gly Lys Met Cys Leu Ser Cys Val Lys Ser Gly Asp Glu Thr Arg
530                 535                 540
Leu Gln Leu Glu Ala Val Asn Ile Thr Asp Leu Ser Glu Asn Arg Lys
545                 550                 555                 560
Gln Asp Lys Arg Phe Ala Phe Ile Arg Ser Asp Ser Gly Pro Thr Thr
                565                 570                 575
Ser Phe Glu Ser Ala Ala Cys Pro Gly Trp Phe Leu Cys Thr Ala Met
            580                 585                 590
Glu Ala Asp Gln Pro Val Ser Leu Thr Asn Met Pro Asp Glu Gly Val
        595                 600                 605
Met Val Thr Lys Phe Tyr Phe Gln Glu Asp Glu
    610                 615

<210> SEQ ID NO 3
<211> LENGTH: 235
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 3

Leu Pro Ala Gln Val Ala Phe Thr Pro Tyr Ala Pro Glu Pro Gly Ser
1               5                   10                  15
Thr Cys Arg Leu Arg Glu Tyr Tyr Asp Gln Thr Ala Gln Met Cys Cys
                20                  25                  30
Ser Lys Cys Ser Pro Gly Gln His Ala Lys Val Phe Cys Thr Lys Thr
            35                  40                  45
Ser Asp Thr Val Cys Asp Ser Cys Glu Asp Ser Thr Tyr Thr Gln Leu
        50                  55                  60
Trp Asn Trp Val Pro Glu Cys Leu Ser Cys Gly Ser Arg Cys Ser Ser
65                  70                  75                  80
```

```
Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp
225                 230                 235

<210> SEQ ID NO 4
<211> LENGTH: 231
<212> TYPE: PRT
<213> ORGANISM: Homo sapiens

<400> SEQUENCE: 4

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205
```

```
Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 5
<211> LENGTH: 152
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 5

Arg Pro Ser Gly Arg Lys Ser Ser Lys Met Gln Ala Phe Arg Ile Trp
1               5                   10                  15

Asp Val Asn Gln Lys Thr Phe Tyr Leu Arg Asn Asn Gln Leu Val Ala
            20                  25                  30

Gly Tyr Leu Gln Gly Pro Asn Val Asn Leu Lys Glu Lys Ile Asp Val
        35                  40                  45

Val Pro Ile Glu Pro His Ala Leu Phe Leu Gly Ile His Gly Gly Lys
    50                  55                  60

Met Cys Leu Ser Cys Val Lys Ser Gly Asp Glu Thr Arg Leu Gln Leu
65                  70                  75                  80

Glu Ala Val Asn Ile Thr Asp Leu Ser Glu Asn Arg Lys Gln Asp Lys
                85                  90                  95

Arg Phe Ala Phe Ile Arg Ser Asp Ser Gly Pro Thr Thr Ser Phe Glu
            100                 105                 110

Ser Ala Ala Cys Pro Gly Trp Phe Leu Cys Thr Ala Met Glu Ala Asp
        115                 120                 125

Gln Pro Val Ser Leu Thr Asn Met Pro Asp Glu Gly Val Met Val Thr
    130                 135                 140

Lys Phe Tyr Phe Gln Glu Asp Glu
145                 150

<210> SEQ ID NO 6
<211> LENGTH: 1467
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 6
atggcgcccg tcgccgtctg ggccgcgctg gccgtcggac tggagctctg ggctgcggcg      60
cacgccttgc cgcccaggt ggcatttaca ccctacgccc cggagccgg gagcacatgc       120 cggctcagag aatactatga ccagacagct cagatgtgct gcagcaaatg ctcgccgggc    180
caacatgcaa agtcttctg taccaagacc tcggacaccg tgtgtgactc ctgtgaggac    240
agcacataca cccagctctg gaactgggtt cccgagtgct tgagctgtgg ctcccgctgt    300
agctctgacc aggtggaaac tcaagcctgc actcgggaac agaaccgcat ctgcacctgc    360
aggcccggct ggtactgcgc gctgagcaag caggaggggt gccggctgtg cgcgccgctg    420
cgcaagtgcc gccgggctt cggcgtggcc agaccaggaa ctgaaacatc agacgtggtg    480
tgcaagccct gtgccccggg gacgttctcc aacacgactt catccacgga tatttgcagg    540
ccccaccaga tctgtaacgt ggtggccatc cctgggaatg caagcatgga tgcagtctgc    600
acgtccacgt cccccacccg gagtatggcc caggggcag tacacttacc ccagccagtg    660
```

-continued

```
tccacacgat cccaacacac gcagccaact ccagaaccca gcactgctcc aagcacctcc    720
ttcctgctcc caatgggccc cagccccca gctgaaggga gcactggcga cgagcccaaa     780
tcttgtgaca aaactcacac atgcccaccg tgcccagcac ctgaactcct ggggggaccg    840
tcagtcttcc tcttcccccc aaaacccaag gacaccctca tgatctcccg gacccctgag    900
gtcacatgcg tggtggtgga cgtgagccac gaagaccctg aggtcaagtt caactggtac    960
gtggacggcg tggaggtgca taatgccaag acaaagccgc gggaggagca gtacaacagc   1020
acgtaccgtg tggtcagcgt cctcaccgtc ctgcaccagg actggctgaa tggcaaggag   1080
tacaagtgca aggtctccaa caaagccctc ccagccccca tcgagaaaac catctccaaa   1140 gccaagggc agccccgaga accacaggtg tacaccctgc ccccatcccg ggatgagctg    1200
accaagaacc aggtcagcct gacctgcctg gtcaaaggct tctatcccag cgacatcgcc   1260
gtggagtggg agagcaatgg gcagccggag aacaactaca agaccacgcc tcccgtgctg   1320
gactccgacg gctccttctt cctctacagc aagctcaccg tggacaagag caggtggcag   1380
caggggaacg tcttctcatg ctccgtgatg catgaggctc tgcacaacca ctacacgcag   1440
aagagcctct ccctgtctcc gggtaaa                                       1467
```

<210> SEQ ID NO 7
<211> LENGTH: 467
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 7

```
Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205
```

```
Pro Glu Pro Ser Thr Ala Pro Ser Thr Ser Phe Leu Leu Pro Met Gly
    210                 215                 220
Pro Ser Pro Pro Ala Glu Gly Ser Thr Gly Asp Glu Pro Lys Ser Cys
225                 230                 235                 240
Asp Lys Thr His Thr Cys Pro Pro Cys Pro Ala Pro Glu Leu Leu Gly
                245                 250                 255
Gly Pro Ser Val Phe Leu Phe Pro Pro Lys Pro Lys Asp Thr Leu Met
                260                 265                 270
Ile Ser Arg Thr Pro Glu Val Thr Cys Val Val Val Asp Val Ser His
            275                 280                 285
Glu Asp Pro Glu Val Lys Phe Asn Trp Tyr Val Asp Gly Val Glu Val
        290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
                340                 345                 350
Glu Lys Thr Ile Ser Lys Ala Lys Gly Gln Pro Arg Glu Pro Gln Val
            355                 360                 365
Tyr Thr Leu Pro Pro Ser Arg Asp Glu Leu Thr Lys Asn Gln Val Ser
        370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
                420                 425                 430
Asp Lys Ser Arg Trp Gln Gln Gly Asn Val Phe Ser Cys Ser Val Met
                435                 440                 445
His Glu Ala Leu His Asn His Tyr Thr Gln Lys Ser Leu Ser Leu Ser
        450                 455                 460
Pro Gly Lys
465

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Tyr Lys Asp Asp Asp Asp Lys
1               5
```

CHIMERIC POLYPEPTIDE AND USE THEREOF

RELATED APPLICATION

This application claims priority to U.S. Provisional Application Ser. No. 60/497,988, filed Aug. 26, 2003, the content of which is incorporated herein by reference in its entirety.

FIELD OF THE INVENTION

The present invention is directed to a chimeric protein therapeutic agent useful in treatment of diseases such as acute and chronic inflammation.

BACKGROUND OF THE INVENTION

Inflammation is the body's defense reaction to injuries such as those caused by mechanical damage, infection or antigenic stimulation. An inflammatory reaction may be expressed pathologically when inflammation is induced by an inappropriate stimulus such as an autoantigen, expressed in an exaggerated manner or persists well after the removal of the injurious agents.

Two important mediators of inflammation reaction are tumor necrosis factor (TNF) and interleukin-1 (IL-1). TNF neutralizer and IL-1 antagonist have been used to treat inflammation-dependent diseases.

Tumor necrosis factor-alpha (CNF alpha) and Tumor necrosis factor beta (INF-beta) are mammalian secreted proteins capable of inducing a wide variety of effects on a large number of cell types. The great similarities in the structural and functional characteristics of these two cytokines have resulted in their collective description as "TNF".

TNF proteins initiate their biological effects on cells by binding to specific TNF receptor (TNFR) proteins expressed on the plasma membrane of a TNF-responsive cell. Two distinct forms of TNFR are known to exist: Type I TNFR (TNFRI), having a molecular weight of approximately 75 kilodaltons, and type II TNFR (TNFRII), having a molecular weight of approximately 55 kilodaltons. TNFRI and TNFRII each bind to both TNF alpha and TNF beta.

TNF antagonists, such as soluble TNFR and TNF binding proteins, bind to TNF and prevent TNF from binding to cell membrane bound TNF receptors. Such proteins were used to suppress biological activities caused by TNF.

The role of TNF in mediated inflammatory diseases has been well established. TNFRII have been proved to be safe and effective clinically for indications of TNF dependent disorders such as rheumatoid arthritis and psoriasis.

One of the most potent inflammatory cytokines is IL-1. IL-1 is manufactured by cells of the macrophage/monocyte lineage, and may be produced in two forms: IL-1 alpha and IL-1 beta. IL-1 proteins initiate their biological effects on cells by binding to specific IL-1 receptor (IL-1R), proteins expressed on the plasma membrane of an IL-1 responsive cell.

IL-1 receptor antagonist (IL-1ra) is a human protein that acts as a natural inhibitor of IL-1. IL-1ra binds to cell membrane bound IL-1 receptors and prevents IL-1 from binding to the same IL-1 receptors. This protein has been used to suppress biological activities caused by IL-1.

In theory, simultaneously neutralizing or blocking two important inflammatory mediators, such as TNF and IL-1, should have the best therapeutic value for treatment of inflammation dependent disorders. However, clinical trial of 242 patients and 24-weeks of concurrent use of a soluble TNFRII and non-glycosylated IL-1ra published by Immunex Inc and Amgen Inc did not increase the efficacy but lead to higher incidence of infection and neutrapenia than that of a soluble TNFRII and IL-1ra as monotherapy.

SUMMARY OF INVENTION

This invention relates to a novel chimeric polypeptide for treating TNF and IL-1 dependent disorders. The chimeric polypeptide includes (1) a TNF neutralizer domain, (2) an IL-1 receptor antagonist domain and (3) a dimerization domain. The three domains are operably linked to each other. The TNF neutralizer domain may include an extracellular domain of human TNFRII; the IL-1 receptor antagonist domain may include IL-1ra; and the dimerization domain may include a human IgG1 Fc fragment or a human immunoglobulin heavy chain constant region. In particular, the IL-1ra is a glycosylated mammalian polypeptide.

In one embodiment, chimeric polypeptide includes, from the N-terminus to the C-terminus, a TNF neutralizer domain, a dimerization domain, and an IL-1 receptor antagonist domain. For example, the chimeric polypeptide may include an extracellular domain of human TNFRII, human IgG1 Fc, and IL-1ra (e.g., SEQ ID NO:2).

In another aspect, the invention features a polynucleotide comprising a sequence encoding a chimeric polypeptide of the invention, as well as a cell producing such a polynucleotide. For example, the cell may be a mammalian cell such as CHO cells, NS0 cells and SP2/0 cells. The polynucleotide and the cell of the invention can be used to produce a chimeric polypeptide of the invention.

A "polynucleotide" or "nucleic acid" refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones, e.g., as these occur in a DNA library such as a cDNA or genomic DNA library. The nucleic acid described above can be used to express a fusion protein of this invention. For this purpose, one can operatively link the nucleic acid to suitable regulatory sequences to generate an expression vector.

The invention further provides a composition containing a chimeric polypeptide or a polynucleotide of the invention and a pharmaceutically acceptable carrier. The composition can be used for treating TNF and IL-1 dependent disorders.

Also within the invention is a method of treating a TNF and IL-1 dependent disorder by administering to a subject in need thereof an effective amount of a composition of the invention. For example, the disorder may be an inflammatory disorder such as rheumatoid arthritis or psoriasis.

The details of one or more embodiments of the invention are set forth in the accompanying drawings and the description below. Other features, objects, and advantages of the invention will be apparent from the description and from the claims.

BRIEF DESCRIPTION OF DRAWINGS

FIG. 1: $1^{st}$ generation of production CHO cell clones of TNFRII-Fc and TNFRII-Fc-IL-1ra chimera: 24 well plate expression in serum-free medium; direct Coomasie blue protein staining; all recombinant proteins are visible ranging 0.5-1.0 ug; loading 10-15 microliters per lane.

FIG. 2: Affinity purification of TNFRII-Fc-IL-1ra chimera: SDS page reduced and non-reduced conditions; Coomasie blue protein staining.

FIG. 3: An example of our trouble-shooting capability: reducing a degradation problem for TNFRII-Fc-IL-1ra chimera by altering the first purification step—HPLC analysis of intact and partially degraded TNFRII-Fc-IL-1ra chimera with TNFRII-Fc control.

FIG. 4: SEC-HPLC analysis of TNFRII-Fc-IL-1ra chimera after formulation and lyophilization.

FIG. 5: IL-1 receptor binding assay indicates that TNFRII-Fc-IL-1ra chimera binds human IL-1 receptor with higher affinity than marketed non-glycosylated IL-1ra (KINERET).

FIG. 6: TNF alpha binding assay indicates that TNFRII-Fc in-house (+ve control) binds to TNF alpha specifically when comparing with −ve control Tie2-Fc.

FIG. 7: TNF alpha binding assay indicates that TNFRII-Fc-IL-1ra chimera binds to TNF alpha specifically to TNF alpha similar to that of TNFRII-Fc (FIG. 6).

FIG. 8: Cell-based TNF alpha neutralization test indicates that similar to marketed TNFRII-Fc (ENBREL), TNFRII-Fc-IL-1ra chimera neutralizes TNF alpha's killing activity on L979 cells.

FIG. 9: Cell-based IL-1 neutralization test indicates that both marketed IL-1ra (KINERET) and TNFRII-Fc-IL-1ra chimera neutralize IL-1's biological activity on D10 cell proliferation. As expected, glycosylated IL-1ra has lower in vitro activity than E-coli made non-glycosylated IL-1ra (KINERET).

DETAILED DESCRIPTION OF THE INVENTION

This invention is based on the discovery of a chimeric polypeptide that can be used for treating TNF and IL-1 dependent disorder. The chimeric polypeptide includes (1) a TNF neutralizer domain, (2) an IL-1 receptor antagonist domain, and (3) a dimerization domain. The three domains are operably linked to each other.

Surprisingly, this chimeric molecule is produced at commercial production level in mammalian hosts using TNFRII-Fc production level as a reference. It contains intact TNF and IL-1 neutralizing activities after the chimerization. In other word, fusion of a large TNFRII-Fc molecule to N-terminus of IL-1ra does not interrupt IL-1ra's IL-1 receptor binding and IL-1 neutralizing activities. Unlike concurrent use of TNFRII-Fc and IL-1ra, this chimeric molecule is distributed more at inflammatory site through systemic administration route, making it an inflammation site directed TNFRII-Fc. Our results further indicate that this chimeric molecule made in mammalian hosts, contains glycosylated IL-1ra, and has a larger molecular weight than those of both TNFRII-Fc and IL-1ra. Therefore it has longer biological life, and less frequent effective injection dose. Due to its inflammation site directed nature and less effective dose and dosing frequency, this chimeric molecule may have less side effects when comparing with that of TNFRII-Fc and concurrent use of TNFRII-Fc and IL-1ra.

A "TNF neutralizer domain" refers to a domain capable of neutralizing TNF, i.e., inhibiting the activity of TNF, e.g., TNF-alpha. For example, a TNF neutralizer domain may include an extracellular domain of human TNFRII, an extracellular domain IL-6 receptor, an antibody to TNF or a TNF receptor, or an antibody to IL-6 or an IL-6 receptor.

TNF neutralizer domains are well known in the art. For example, U.S. Pat. No. 5,605,690. discloses TNF receptors (TNFRs) having amino acid sequences which are substantially similar to the native mammalian TNF receptor or TNF binding protein amino acid sequences, and which are capable of binding TNF molecules and inhibiting TNF from binding to cell membrane bound TNFR.

Two distinct types of TNFR are known to exist as mentioned earlier: Type I TNFR (TNFRI) and Type II TNFR (TNFRII). The preferred TNFRs of the present invention are soluble forms of TNFRI and TNFRII, as well as soluble TNF binding proteins. Soluble TNFR molecules include, for example, analogs or subunits of native proteins having at least 20 amino acids and which exhibit at least some biological activity in common with TNFRI, TNFRII or TNF binding proteins. Soluble TNFR constructs are devoid of a transmembrane region (and are secreted from the cell) but retain the ability to bind TNF. Various bioequivalent protein and amino acid analogs have an amino acid sequence corresponding to all or part of the extracellular region of a native TNFR, for example, huTNFRI.DELTA.235, huTNFRI.DELTA.185 and huTNFRI.DELTA.163, or amino acid sequences substantially similar to the sequences of amino acids 1-163, amino acids 1-185, or amino acids 1-235 of SEQ ID NO:1 disclosed in U.S. Pat. No. 5,605,690, and which are biologically active in that they bind to TNF ligand. Equivalent soluble TNFRs include polypeptides which vary from these sequences by one or more substitutions, deletions, or additions, and which retain the ability to bind TNF or inhibit TNF signal transduction activity via cell surface bound TNF receptor proteins, for example huTNFRI.DELTA.x, wherein x is selected from the group consisting of any one of amino acids 163-235 of SEQ ID NO:1 disclosed in U.S. Pat. No. 5,605,690. Analogous deletions may be made to muTNFR. Inhibition of TNF signal transduction activity can be determined by transfecting cells with recombinant TNFR DNAs to obtain recombinant receptor expression. The cells are then contacted with TNF and the resulting metabolic effects examined. If an effect results which is attributable to the action of the ligand, then the recombinant receptor has signal transduction activity. Exemplary procedures for determining whether a polypeptide has signal transduction activity are disclosed by Idzerda et al., J. Exp. Med. 171:861 (1990); Curtis et al., Proc. Natl. Acad. Sci. U.S.A. 86:3045 (1989); Prywes et al., EMBO J. 5:2179 (1986) and Chou et al., J. Biol. Chem. 262:1842 (1987). Alternatively, primary cells or cell lines which express an endogenous TNF receptor and have a detectable biological response to TNF could also be utilized.

The nomenclature for TNFR analogs as used herein follows the convention of naming the protein (e.g., TNFR) preceded by either "hu" (for human) or "mu" (for murine) and followed by a DELTA. (to designate a deletion) and the number of the C-terminal amino acid. For example, huTNFR.DELTA.235 refers to human TNFR having Asp.sup.235 as the C-terminal amino acid (i.e., a polypeptide having the sequence of amino acids 1-235 of SEQ ID NO:1 disclosed in U.S. Pat. No. 5,605,690). In the absence of any human or murine species designation, TNFR refers generically to mammalian TNFR. Similarly, in the absence of any specific designation for deletion mutants, the term TNFR means all forms of TNFR, including routants and analogs which possess TNFR biological activity.

"Biologically active," as used throughout the specification as a characteristic of TNF receptors, means that a particular molecule shares sufficient amino acid sequence similarity with the embodiments of the present invention disclosed herein to be capable of binding detectable quantities of TNF, transmitting a TNF stimulus to a cell, for example, as a component of a hybrid receptor construct, or cross-reacting with anti-TNFR antibodies raised against TNFR from natural (i.e., nonrecombinant) sources. Preferably, biologically active TNF receptors within the scope of the present invention are capable of binding greater than 0.1 nmoles TNF per nmole receptor, and most preferably, greater than 0.5 nmole TNF per umole receptor in standard binding assays.

In preferred aspects of the present invention, the INF neutralizers are selected from the group consisting of soluble human TNFRI and TNFR II. The pCAV/NOT-TNFR vector, containing the human TNFRI cDNA clone 1, was used to express and purify soluble human TNFRI. pCAV/NOT-TNFR has been deposited with the American Type Culture Collection, 12301 Parklawn Drive, Rockville, Md. 20852, U.S.A. (Accession No. 68088) under the name pCAV/NOT-TNFR.

Like most mammalian genes, mammalian TNF receptors are presumably encoded by multi-exon genes. Alternative mRNA constructs which can be attributed to different mRNA splicing events following transcription, and which share large regions of identity or similarity with the cDNAs disclosed in U.S. Pat. No. 5,605,690 may also be used.

Other mammalian TNFR cDNAs may be isolated by using an appropriate human TNFR DNA sequence as a probe for screening a particular mammalian cDNA library by cross-species hybridization. Mammalian TNFR used in the present invention includes, by way of example, primate, human, murine, canine, feline, bovine, ovine, equine and porcine TNFR. Mammalian TNFRs can be obtained by cross species hybridization, using a single stranded cDNA derived from the human TNFR DNA sequence as a hybridization probe to isolate TNFR cDNAs from mammalian cDNA libraries.

Functional equivalents of TNFR which may be used in the present invention A "functional equivalent" refers to a polypeptide derived from the TNFR polypeptide, e.g., fusion proteins or proteins having one or more point mutations, insertions, deletions, truncations, or combination thereof. It retains substantially the activity of the TNFR polypeptide, i.e., the ability to bind to TNF. The isolated polypeptide can contain SEQ ED NO: 3 or a fragment of SEQ ID NO: 3, or can be SEQ ID NO: 3 or a fragment of SEQ ID NO: 3.

The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to TNFR amino acid side chains or at the N- or C-termini. Other derivatives of TNFR include covalent or aggregative conjugates of TNFR or its fragments with other proteins or polypeptides, such as by synthesis in recombinant culture as N-terminal or C-terminal fusions. For example, the conjugated peptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast .alpha.-factor leader). TNFR protein fusions can comprise peptides added to facilitate purification or identification of TNFR (e.g., poly-His). The amino acid sequence of TNF receptor can also be linked to the peptide Asp-Tyr-Lys-Asp-Asp-Asp-Asp-Lys (DYKDDDDK) (SEQ ID NO: 8) (Hopp et al., Bio/Technology 6:1204, 1988.) The latter sequence is highly antigenic and provides an epitope reversibly bound by a specific monoclonal antibody, enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradation in E. coli.

TNFR with or without associated native-pattern glycosylation may also be used. TNFR expressed in yeast or mammalian expression systems, e.g., COS-7 cells, may be similar or slightly different in molecular weight and glycosylation pattern than the native molecules, depending upon the expression system. Expression of TNFR DNAs in bacteria such as E. coli provides non-glycosylated molecules. Functional mutant analogs of mammalian TNFR having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-A.sub.1-Z, where A.sub.1 is any amino acid except Pro, and Z is Ser or Thr. In this sequence, Asn provides a side chain amino group for covalent attachment of carbohydrate. Such a site can be eliminated by substituting another amino acid for Asn or for residue Z, deleting Asn or Z, or inserting a non-Z amino acid between A.sub.1 and Z, or an amino acid other than Asn between Asn and A.sub.1.

TNFR derivatives may also be obtained by mutations of TNFR or its subunits. A TNFR mutant, as referred to herein, is a polypeptide homologous to TNFR but which has an amino acid sequence different from native TNFR because of a deletion, insertion or substitution.

Bioequivalent analogs of TNFR proteins may be constructed by, for example, making various substitutions of residues or sequences or deleting terminal or internal residues or sequences not needed for biological activity. For example, cysteine residues can be deleted (e.g., Cys.sup.178) or replaced with other amino acids to prevent formation of unnecessary or incorrect intramolecular disulfide bridges upon renaturation. Other approaches to mutagenesis involve modification of adjacent dibasic amino acid residues to enhance expression in yeast systems in which KEX2 protease activity is present. Generally, substitutions should be made conservatively; i.e., the most preferred substitute amino acids are those having physiochemical characteristics resembling those of the residue to be replaced. Similarly, when a deletion or insertion strategy is adopted, the potential effect of the deletion or insertion on biological activity should be considered. Substantially similar polypeptide sequences, as defined above, generally comprise a like number of amino acids sequences, although C-terminal truncations for the purpose of constructing soluble TNFRs will contain fewer amino acid sequences. In order to preserve the biological activity of TNFRs, deletions and substitutions will preferably result in homologous or conservatively substituted sequences, meaning that a given residue is replaced by a biologically similar residue. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Moreover, particular amino acid differences between human, murine and other mammalian TNFRs are suggestive of additional conservative substitutions that may be made without altering the essential biological characteristics of TNFR.

Subunits of TNFR may be constructed by deleting terminal or internal residues or sequences. Particularly preferred sequences include those in which the transmembrane region and intracellular domain of TNFR are deleted or substituted with hydrophilic residues to facilitate secretion of the receptor into the cell culture medium. The resulting protein is referred to as a soluble TNFR molecule which retains its ability to bind TNF. A particularly preferred soluble TNFR construct is TNFRI.DELTA.235 (the sequence of amino acids 1-235 of SEQ ID NO:1 disclosed in U.S. Pat. No. 5,605,690), which comprises the entire extracellular region of TNFRI, terminating with Asp.sup.235 immediately adjacent the transmembrane region. Additional amino acids may be deleted from the transmembrane region while retaining TNF binding activity. For example, huTNFRI.DELTA.183 which comprises the sequence of amino acids 1-183 of SEQ ID NO: 1, and INFRI.DELTA.163 which comprises the sequence of amino acids 1-163 of SEQ ID NO: 1 disclosed in U.S. Pat. No. 5,605,690, retain the ability to bind TNF ligand. TNFRI.DELTA.142, however, does not retain the ability to bind TNF ligand. This suggests that one or both of Cys-.sup.157 and Cys.sup.163 is required for formation of an intramolecular disulfide bridge for the proper folding of TNFRI. Cys.sup.178, which was deleted without any apparent adverse effect on the ability of the soluble TNFRI to bind TNF, does not appear to be essential for proper folding of TNFRI. Thus, any deletion C-terminal to Cys.sup.163 would be expected to result in a biologically active soluble TNFRI. The present invention contemplates use of such soluble TNFR constructs corresponding to all or part of the extracellular region of TNFR terminating with any amino acid after Cys.sup.163. Other C-terminal deletions, such as TNPRI.DELTA.157, may be made as a matter of convenience by cutting TNFR cDNA with appropriate restriction enzymes and, if necessary, reconstructing specific sequences with synthetic oligonucleotide linkers. Soluble TNFR with N-terminal deletions may also be used in the present invention. For example, the N-terminus of TNFRI may begin with Leu.sup.1, Pro.sup.2 or Ala.sup.3 without significantly affecting the ability of TNFRI to effectively act as a TNF antagonist. The resulting soluble TNFR constructs are then inserted and expressed in appropriate expression vectors and assayed for the ability to bind TNF.

Mutations in nucleotide sequences constructed for expression of analog TNFR must, of course, preserve the reading frame phase of the coding sequences and preferably will not create complementary regions that could hybridize to produce secondary mRNA structures such as loops or hairpins which would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at the target codon and the expressed TNFR mutants screened for the desired activity.

Not all mutations in the nucleotide sequence which encodes TNFR will be expressed in the final product, for example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known *E. coli* preference codons for *E. coli* expression.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462 disclose suitable techniques, and are incorporated by reference herein.

Antibodies to TNF or TNFRs may be used as antibody therapeutics to treat TNF dependent diseases. These antibodies contain immunoglobulin heavy chain constant region similar to a dimerized IgG Fc fragment at its C-terminus and two TNF or TNFR binding Fab domains at its N-terminus.

The activity of these antibodies may be determined by using TNF dependent cells such as L979 cell (ATTC). TNF-dependent cells can be killed by adding effective dose of recombinant TNF alpha. This TNF-dependent activity can be neutralized by addition of these antibodies into the reaction. The activity of these antibodies may also be determined by using TNF in vitro binding assay in 96-well plate.

Soluble IL-6 receptors or antibodies to IL-6 or IL-6R with IgG heavy chain constant region similar to a dimerized IgG Fc fragment at their C-terminus may be used to replace TNFRII of this chimeric molecule. The activity of these molecules may be determined by using IL-6 receptor in vitro binding assay in 96-well plate. The activity may also be determined by using recombinant IL-6 and IL-6-dependent D10 cells.

An "interleukin-1 receptor antagonist domain" refers to a domain capable of specifically binding to IL-1 receptor and preventing activation of cellular receptors to IL-1. Examples of interleukin-1 receptor antagonists include IL-1ra (U.S. Pat. No. 6,096,728) and anti-IL-1 receptor monoclonal antibodies (EP 623674), as well as their functional equivalents, i.e., polypeptides derived from IL-1ra or anti-IL-1 receptor monoclonal antibodies, e.g., fusion proteins or proteins having one or more point mutations, insertions, deletions, truncations, or combination thereof. They retain substantially the activity of specifically binding to IL-1 receptor and preventing activation of cellular receptors to IL-1. They can contain SEQ ID NO: 5 or a fragment of SEQ ID NO: 5. Preferably, the IL-1ra is a glycosylated mammalian polypeptide. The activity of an Interleukin-1 receptor antagonist may be determined by cell-based IL-1 neutralization assay using IL-1 dependent D10 cells (see Example 4).

Preferred IL-1ra proteins are described in U.S. Pat. No. 5,075,222 (referred to herein as the '222 patent); WO 91/08285; WO 91/17184; AU 9173636; WO 92/16221 and WO 96/22793, the disclosures of which are incorporated herein by reference. The proteins include glycosylated as well as non-glycosylated IL-1 receptor antagonists.

Specifically, three useful forms of IL-1ra and variants thereof are disclosed and described in the '222 patent. The first of these, IL-1ra.alpha., is characterized as a 22-23 kD molecule on SDS-PAGE with an approximate isoelectric point of 4.8, eluting from a Mono Q FPLC column at around 52 mM NaCl in Tris buffer, pH 7.6. The second, IL-1ra.beta., is characterized as a 22-23 kD protein, eluting from a Mono Q column at 48 mM NaCl. Both IL-1ra alpha and IL-1ra.beta are glycosylated. The third, IL-1rax, is characterized as a 20 kD protein, eluting from a Mono Q column at 48 mM NaCl, and is non-glycosylated. All three of these inhibitors possess similar functional and immunological activities.

The present invention also includes modified forms of IL-1ra. The modified forms of IL-1ra as used herein include variant polypeptides in which amino acids have been (1) deleted from ("deletion variants"), (2) inserted into ("addition variants") or (3) substituted for ("substitution variants") residues within the amino acid sequence of IL-1ra.

For IL-1ra deletion variants, each polypeptide may typically have an amino sequence deletion ranging from about 1 to 30 residues, more typically from about 1 to 10 residues and most typically from about 1 to 5 contiguous residues. N-terminal, C-terminal and internal intrasequence deletions are contemplated. Deletions within the IL-1ra amino acid sequence may be made in regions of low homology with the sequences of other members of the IL-1 family. Deletions within the IL-1ra amino acid sequence may be made in areas of substantial homology with the sequences of other members of the IL-1 family and will be more likely to significantly modify the biological activity.

For IL-1ra addition variants, each polypeptide may include an amino- and/or carboxyl-terminal fusion ranging in length from one residue to one hundred or more residues, as well as internal intrasequence insertions of single or multiple amino acid residues. Internal additions may range typically from about 1 to 10 amino acid residues, more typically from about 1 to 5 amino acid residues and most typically from about 1 to 3 amino acid residues.

Amino-terminus addition variants include the addition of a methionine (for example, as an artifact of the direct expression of the protein in bacterial recombinant cell culture) or an additional amino acid residue or sequence. A further example of an amino-terminal insertion includes the fusion of a signal sequence, as well as or with other pre-pro sequences, to facilitate the secretion of protein from recombinant host cells. Each polypeptide may comprise a signal sequence selected to be recognized and processed, i.e., cleaved by a signal peptidase, by the host cell. For prokaryotic host cells that do not recognize and process the native IL-1ra signal sequence, each polypeptide may comprise a prokaryotic signal sequence selected, for example, from the group of the alkaline phosphatase, penicillinase or heat-stable enterotoxin II leaders. For yeast cells, each polypeptide may have a signal sequence selected, for example, from the group of the yeast invertase, alpha factor or acid phosphatase leader sequences. For mammalian cell expression, each polypeptide may have the native signal sequence of IL-1ra, although other mammalian signal sequences may be suitable, for example, sequences derived from other IL-1 family members.

For IL-1ra substitution variants, each such polypeptide may have at least one amino acid residue in IL-1ra removed and a different residue inserted in its place. Substitution variants include allelic variants, which are characterized by naturally-occurring nucleotide sequence changes in the species population that may or may not result in an amino acid change. One skilled in the art can use any information known about the binding or active site of the polypeptide in the selection of possible mutation sites. Exemplary substitution variants are taught in WO 91/17184, WO 92/16221, and WO 96/09323.

One method for identifying amino acid residues or regions for mutagenesis of a protein is called "alanine scanning mutagenesis" (Cunningham and Wells (1989), Science, 244: 1081-1085, the disclosure of which is hereby incorporated by reference). In this method, an amino acid residue or group of target residues of a protein is identified (e.g., charged residues such as Arg, Asp, His, Lys and Glu) and replaced by a neutral or negatively-charged amino acid (most preferably alanine or polyalanine) to effect the interaction of the amino acids with the surrounding aqueous environment in or outside the cell. Those residues demonstrating functional sensitivity to the substitutions are then refined by introducing additional or alternate residues at the sites of substitution. Thus, the site for introducing an amino acid sequence modification is predetermined and, to optimize the performance of a mutation at a given site, alanine scanning or random mutagenesis may be conducted and the resulting variant polypeptide is screened for the optimal combination of desired activity and degree of activity.

The sites of greatest interest for substitutional mutagenesis include sites where the amino acids found in IL-ra are substantially different in terms of side-chain bulk, charge and/or hydrophobicity from IL-1ra-like proteins such as IL-1ra's of other various species or of other members of the IL-1 family. Other sites of interest include those in which particular residues of IL-1ra are identical with those of such IL-1ra-like proteins. Such positions are generally important for the biological activity of a protein. Initially, these sites are modified by substitution in a relatively conservative manner. Such conservative substitutions are shown in Table 1 under the heading of "Preferred Substitutions". If such substitutions result in a change in biological activity, then more substantial changes (Exemplary Substitutions) are introduced and/or other additions/deletions may be made and the resulting polypeptides screened.

TABLE 1

Amino Acid Substitutions

| Original Residue | Preferred Substitutions | Exemplary Substitutions |
| --- | --- | --- |
| Ala (A) | Val | Val; Leu; Ile |
| Arg (R) | Lys | Lys; Gln; Asn |
| Asn (N) | Gln | Gln; His; Lys; Arg |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Arg | Asn; Gln; Lys; Arg |
| Ile (I) | Leu | Leu; Val; Met; Ala; Phe; norleucine |
| Leu (L) | Ile | norleucine; Ile; Val; Met; Ala; Phe |
| Lys (K) | Arg | Arg; Gln; Asn |
| Met (M) | Leu | Leu; Phe; Ile |
| Phe (F) | Leu | Leu; Val; Ile; Ala |
| Pro (P) | Gly | Gly |
| Ser (S) | Thr | Thr |
| Thr (T) | Ser | Ser |
| Trp (W) | Tyr | Tyr |
| Tyr (Y) | Phe | Trp; Phe; Thr; Ser |
| Val (V) | Leu | Ile; Leu; Met; Phe; Ala; norleucine |

Conservative modifications to the amino acid sequence (and the corresponding modifications to the encoding nucleic acid sequence) of IL-1ra are expected to produce proteins having similar functional and chemical characteristics. In contrast, substantial modifications in the functional and/or chemical characteristics of IL-1ra may be accomplished by selecting substitutions that differ significantly in their effect on maintaining (a) the structure of the polypeptide backbone in the area of the substitution, for example, as a sheet or helical conformation, (b) the charge or hydrophobicity of the protein at the target site or (c) the bulk of the side chain. Naturally-occurring residues are divided into groups based on common side chain properties:

1) hydrophobic: norleucine, Met, Ala, Val, Leu, Ile;

2) neutral hydrophilic: Cys, Ser, Thr;

3) acidic: Asp, Glu;

4) basic: Asn, Gln, His, Lys, Arg;

5) aromatic: Trp, Tyr, Phe; and 6) residues that influence chain orientation: Gly, Pro.

Non-conservative substitutions may involve the exchange of a member of one of these groups for another. Such substituted residues may be introduced into regions of IL-1ra that are homologous or non-homologous with other IL-1 family members.

Specific mutations in the sequence of IL-1ra may involve substitution of a non-native amino acid at the N-terminus, C-terminus or at any site of the protein that is modified by the addition of an N-linked or O-linked carbohydrate. Such modifications may be of particular utility, such as in the addition of an amino acid (e.g., cysteine), which is advantageous for the linking of a water soluble polymer to form a derivative. Further, the sequence of IL-1ra may be modified to add glycosylation sites or to delete N-linked or O-linked glycosylation sites. An asparagine-linked glycosylation recognition site comprises a tripeptide sequence which is specifically recognized by appropriate cellular glycosylation enzymes. These tripeptide sequences are either Asn-Xaa-Thr or Asn-Xaa-Ser, where Xaa can be any amino acid other than Pro.

In a specific embodiment, the variants are substantially homologous to the amino acid of IL-1ra (SEQ ID NO:5). The term "substantially homologous" as used herein means a degree of homology that is preferably in excess of 70%, more preferably in excess of 80%, even more preferably in excess of 90% or most preferably even 95%. The percentage of homology as described herein is calculated as the percentage of amino acid residues found in the smaller of the two sequences which align with identical amino acid residues in the sequence being compared when four gaps in a length of 100 amino acids may be introduced to assist in that alignment, as set forth by Dayhoff in Atlas of Protein Sequence and Structure, 5:124 (1972), National Biochemical Research Foundation, Washington, D.C., the disclosure of which is hereby incorporated by reference. Also included as substantially homologous are variants of IL-1ra which may be isolated by virtue of cross-reactivity with antibodies to the amino acid sequence of SEQ ID NO:5 or whose genes may be isolated through hybridization with a DNA encoding SEQ ID NO:5 or with segments thereof.

IL-1ra variants may be prepared by introducing appropriate nucleotide changes into the DNA encoding variants of IL-1ra or by in vitro chemical synthesis of the desired variants of IL-1ra. It will be appreciated by those skilled in the art that many combinations of deletions, insertions and substitutions can be made, provided that the final variants of IL-1ra are biologically active.

Mutagenesis techniques for the replacement, insertion or deletion of one or more selected amino acid residues are well known to one skilled in the art (e.g., U.S. Pat. No. 4,518,584, the disclosure of which is hereby incorporated by reference). There are two principal variables in the construction of each amino acid sequence variant, the location of the mutation site and the nature of the mutation. In designing each variant, the location of each mutation site and the nature of each mutation will depend on the biochemical characteristic(s) to be modified. Each mutation site can be modified individually or in series, e.g., by (1) substituting first with conservative amino acid choices and then with more radical selections, depending upon the results achieved, (2) deleting the target amino acid residue or (3) inserting one or more amino acid residues adjacent to the located site.

A "dimerization domain" refers to a domain capable of engaging two copies of a polypeptide of the invention in one molecule. For example, a dimerization domain may include a dimerized IgG Fc fragment or human IgG heavy chain constant region. An example of such a Fc fragment includes SEQ ID No:4.

IgG Fc fragment dimmerizes through its cystaine residues for formation of inter-chain disulfide bonds (covalent). Sometime non-covalent dimerization also occurs without involving disulfide bond. Dimerized IgG Fc fragment in this chimeric molecule is capable of presenting two functional TNFRII molecules at its N-terminus and two functional IL-1ra molecules at its C-terminus. This arrangement increases in vivo receptor/ligand binding chances for neutralizing both TNF alpha and IL-1 receptors.

The activity of a covalent dimerization through disulfide bond may be determined by using reduced and non-reduced SDS page electroporesis. Molecular weight of the protein should be reduced in half when reduced condition is used. Non-covalent dimerization may be determined by using native and denatured conditions for electroporesis. Molecular weight of the protein should be reduced in half when denatured condition is used.

In a polypeptide of the invention, the TNF neutralizer domain, dimerization domain, and IL-1 receptor antagonist domain are operably linked. As used herein, "operably linked" refers to the structural configuration of the polypeptide that does not interfere with the activities of each domain, i.e., the TNF neutralizer domain retains its capability of neutralizing TNF, the interleukin-1 receptor antagonist domain retains its capability of specifically binding IL-1 receptor and preventing activation of cellular receptors to IL-1, and the dimerization domain retains its capability of engaging two copies of a polypeptide of the invention in one molecule and presenting two functional TNFRII molecules at its N-terminus and two functional IL-1ra molecules at its C-terminus.

For example, a chimeric polypeptide of the invention may include, from the N-terminus to the C-terminus, a TNF neutralizer domain, a dimerization domain, and an IL-1 receptor antagonist domain. An example of such a TNF neutralizer domain includes SEQ ID NO:3. Specifically, the chimeric polypeptide includes an extracellular domain of human TNFRII, human IgG1 Fc, and IL-1ra. An example of such a chimeric polypeptide includes SEQ ID NO:2.

The invention also provides an isolated polynucleotide containing a DNA sequence encoding a chimeric polypeptide of the invention. Such a polynucleotide may be constructed using recombinant DNA technology well known in the art. For example, a polynucleotide of the invention may be a vector containing a DNA sequence encoding a chimeric polypeptide of the invention. The vector can be used for production of the polypeptide.

As used herein, the term "vector" refers to a polynucleotide capable of transporting another polynucleotide to which it has been linked. Various types of vectors are well known in the art. See, e.g., U.S. Pat. No. 6,756,196. One type of vector is a "plasmid", which refers to a circular double stranded DNA loop into which additional DNA'segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operatively linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a polynucleotide of the invention in a form suitable for expression of the polynucleotide in a host cell, which means that the recombinant expression vectors include one or more regulatory sequences, selected on the basis of the host cells to be used for expression, which is operatively linked to the polynucleotide sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or polypeptides, encoded by polynucleotides as described herein.

The recombinant expression vectors of the invention can be designed for expression of a polypeptide of the invention in prokaryotic or eukaryotic cells, e.g., bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

In one embodiment, a polynucleotide of the invention is expressed in mammalian cells using a mammalian expression vector. Examples of mammalian expression vectors include pCDM8 (Seed (1987) Nature 329:840), pCI (Promega), and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al. eds., Molecular Cloning: A Laboratory Manual. 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the polynucleotide preferentially in a particular cell type (e.g., tissue-specific regulatory elements are used to express the polynucleotide). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374-379) and the alpha-fetoprotein promoter (Campes and Tilghman (1989) Genes Dev. 3:537-546).

Another aspect of the invention pertains to host cells into which a recombinant expression vector of the invention or isolated polynucleotide molecule of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a polypeptide of the invention can be expressed in bacterial cells such as E. coli, insect cells, yeast or mammalian cells (such as Chinese hamster ovary cells (CHO) or NS0 cells). Other suitable host cells are known to those skilled in the art.

Vector DNA or an isolated polynucleotide molecule of the invention can be introduced into prokaryotic or eukaryotic cells via conventional transformation or transfection techniques. As used herein, the terms "transformation" and "transfection" are intended to refer to a variety of art-recognized techniques for introducing foreign polynucleotide (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In some cases vector DNA is retained by the host cell. In other cases the host cell does not retain vector DNA and retains only an isolated polynucleotide molecule of the invention carried by the vector. In some cases, and isolated polynucleotide molecule of the invention is used to transform a cell without the use of a vector.

In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Polynucleotide encoding a selectable marker can be introduced into a host cell on the same vector as that encoding a polypeptide of the invention or can be introduced on a separate vector. Cells stably transfected with the introduced polynucleotide can be identified by drug selection (e.g., cells that have incorporated the selectable marker gene will survive, while the other cells die).

A host cell of the invention, such as a prokaryotic or eukaryotic host cell in culture, can be used to produce (i.e., express) a polypeptide of the invention. Accordingly, the invention further provides methods for producing a polypeptide of the invention using the host cells of the invention. In one embodiment, the method comprises culturing the host cell of the invention (into which a recombinant expression vector or isolated polynucleotide molecule encoding a polypeptide of the invention has been introduced) in a suitable medium such that the polypeptide is produced. In another embodiment, the method further comprises isolating the polypeptide from the medium or the host cell.

A polypeptide of the invention can be incorporated into pharmaceutical compositions suitable for administration. Such compositions typically comprise the polypeptide and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the polypeptide in the required amount in an appropriate solvent with one or a combination of ingredients enumerated above, as required, followed by filtered sterilization. Generally, dispersions are prepared by incorporating the polypeptide into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the polypeptide can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compositions can also be prepared in the form of suppositories (e.g., with conventional suppository bases such as cocoa butter and other glycerides) or retention enemas for rectal delivery.

In one embodiment, the polypeptide is prepared with carriers that will protect the polypeptide against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the polypeptide and the particular therapeutic effect to be achieved, and the limitations inherent in the art of compounding such a polypeptide for the treatment of individuals.

The polypeptide of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

The invention further provides a method of treating TNF and IL-1 dependent disorders, including administering to a subject in need thereof an effective amount of a composition of the invention. A "TNF and IL-1 dependent disorder" refers to a disorder that is associated with an abnormal level of the gene expression or activity of TNF or IL-1. Examples of such a disease include, but are not limited to, acute and chronic inflammation (e.g., inflammatory conditions of a joint such as osteoarthritis, psoriatic arthritis and/or rheumatoid arthritis); psoriasis; acute hepatitis, cardiovascular diseases, brain injury as a result of trauma, epilepsy, hemorrhage or stroke; and graft versus host disease.

A subject to be treated may be identified as being in need of treatment for TNF and IL-1 dependent disorders. Identifying a subject in need of such treatment can be in the judgment of a subject or a health care professional, and can be subjective (e.g., opinion) or objective (e.g., measurable by a test or diagnostic method). The term "treating" is defined as administration of a substance to a subject with the purpose to cure, alleviate, relieve, remedy, prevent, or ameliorate a disorder, symptoms of the disorder, a disease state secondary to the disorder, or predisposition toward the disorder. An "effective amount" is an amount of the substance that is capable of producing a medically desirable result as delineated herein in a treated subject. The medically desirable result may be objective (i.e., measurable by some test or marker) or subjective (i.e., subject gives an indication of or feels an effect).

The effective amount of a composition of the invention is between 2.5 and 300 mg per person, 1-4 times every two weeks. The effective amount can be any specific amount within the aforementioned range. The effective amount is useful in a monotherapy or in combination therapy for the treatment of TNF and IL-1 dependent disorders. As the skilled artisan will appreciate, lower or higher doses than those recited above may be required. Effective amounts and treatment regimens for any particular subject (e.g., a mammal such as human) will depend upon a variety of factors, including the activity of the specific extract or its ingredients employed, the age, body weight, general health status, sex, diet, time of administration, rate of excretion, drug combination, the severity and course of the disease, condition or symptoms, the subject's disposition to the disease, condition or symptoms, and the judgment of the treating physician or veterinarian.

The examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLES

Example 1

Construction and Expression of TNFRII-Fc-IL-1ra and Control TNFRII-Fc

The constructs described in SEQ ID NO:1, 6) have been successfully constructed, sequenced, and expressed in mammalian cell lines. Expression titers in serum-free medium in 24-well plate are 50 mg-100 mg/L (FIG. 1) respectively for native signal—human TNFRII extracellular domain—human IgG1 Fc gene—human IL-1ra (SEQ ID No:1) as well as native signal—human TNFRII extracellular domain—human IgG1 Fc gene (SEQ ID No:6). Higher expression of TNFRII-Fc-IL-1ra than TNFRII-Fc in CHOK1 cells (estimated by direct Coomasie blue protein staining to conditional medium) has been found in our recent production clone screening experiments.

Sequence Listing (1) General Information:
  (i) Applicant: Hui, Mizhou.
  (ii) Title of invention: A novel method of treating TNF and IL-1 dependent related application.
  (iii) Number of sequence: 7.
  (iv) Correspondence address:
    (A) Amprotien Corporation
    (B) Street: 355 N Lantana Street #220
    (C) City: Camarillo
    (D) State: California
    (E) Country: United States
    (F) ZIP: 93010

(2) Information for SEQ ID No: 1:
  (i) Sequence characteristics: (A) Length: 1923 bp; (B) Type: nucleic acid; (C) Strandedness: single; (D) Topology: linear.
  (ii) Molecular Type: cDNA
  (iii) Anti-sense: no.
  (iv) Original source: homo sapiens.
  (v) Immediate source: synthetic.
  (vi) Feature: full length coding sequence.
  (vii) Feature: signal peptide 1-66.
  (viii) Sequence description: SEQ ID No:1: (full length nucleotide coding sequence of TNFRII-Fc4L-1ra without stop codon),

```
atggcgcccgtcgccgtctgggccgcgctggccgtcggactggagctctgggctgcggcgcacgccttgcccgcc caggtggcatttacaccctacgccccggagcccgggagcacatgccggctcagagaatactatgaccagacagctc agatgtgctgcagcaaatgctcgccgggccaacatgcaaaagtcttctgtaccaagacctcggacaccgtgtgtgact cctgtgaggacagcacatacacccagctctggaactgggttcccgagtgcttgagctgtggctcccgctgtagctctg accaggtggaaactcaagcctgcactcgggaacagaaccgcatctgcacctgcaggcccggctggtactgcgcgc tgagcaagcaggagggtgccggctgtgcgcgccgctgcgcaagtgccgcccgggcttcggcgtggccagacca ggaactgaaacatcagacgtggtgtgcaagccctgtgccccggggacgttctccaacacgacttcatccacggatatt tgcaggccccaccagatctgtaacgtggtggccatccctgggaatgcaagcatggatgcagtctgcacgtccacgtc ccccacccggagtatggccccaggggcagtacacttaccccagccagtgtccacacgatcccaacacacgcagcc aactccagaacccagcactgctccaagcacctccttcctgctcccaatgggcccagcccccagctgaagggagc actggcgacgagcccaaatcttgtgacaaaactcacacatgcccaccgtgcccagcacctgaactcctgggggac cgtcagtcttcctcttccccccaaaacccaaggacacccctcatgatctcccggacccctgaggtcacatgcgtggtgg tggacgtgagccacgaagaccctgaggtcaagttcaactggtacgtggacggcgtggaggtgcataatgccaagac aaagccgcgggaggagcagtacaacagcacgtaccgtgtggtcagcgtcctcaccgtcctgcaccaggactggct gaatggcaaggagtacaagtgcaaggtctccaacaaagcccteccagcccccatcgagaaaaccatctccaaagcc aaagggcagccccgagaaccacaggtgtacaccctgcccccatcccgggatgagctgaccaagaaccaggtcag cctgacctgcctggtcaaaggcttctatcccagcgacatcgccgtggagtgggagagcaatgggcagccggagaa caactacaagaccacgcctcccgtgctggactccgacggctccttcttcctctacagcaagctcaccgtggacaaga gcaggtggcagcaggggaacgtcttctcatgctccgtgatgcatgaggctctgcacaaccactacacgcagaagag cctctccctgtctccgggtaaacgaccctctgggagaaaatccagcaagatgcaagccttcagaatctgggatgttaa ccagaagaccttctatctgaggaacaaccaactagttgctggatacttgcaaggaccaaatgtcaatttaaaagaaaag atagatgtggtacccattgagcctcatgctctgttcttgggaatccatggagggaagatgtgcctgtcctgtgtcaagtct ggtgatgagaccagactccagctggaggcagttaacatcactgacctgagcgagaacagaaagcaggacaagcgc ttcgccttcatccgctcagacagtggccccaccaccagttttgagtctgccgcctgccccggttggttcctctgcacag cgatggaagctgaccagcccgtcagcctcaccaatatgcctgacgaaggcgtcatggtcaccaaattctacttccag gaggacgag
```

(2) Information for SEQ ID No:2:
(i) Sequence characteristics: (A) Length: 619 amino acids; (B) Type: amino acid; (C) Topology: linear.
(ii) Molecular type: protein.
(iii) Sequence description: SEQ ID No:2: (translated mature amino acid sequence of TNFRII-Fc-IL-1ra)

LPAQVAFTPYAPEPGSTCRLREYYDQTAQMCCSKCSPGQHAKVFCTKTSD
TVCDSCEDSTYTQLWNWVPECLSCGSRCSSDQVETQACTREQNRICTCRP
GWYCALSKQEGCRLCAPLRKCRPGFGVARPGTETSDVVCKPCAPGTFSNT
TSSTDICRPHQICNVVAIPGNASMDAVCTSTSPTRSMAPGAVHLPQPVST
RSQHTQPTPEPSTAPSTSFLLPMGPSPPAEGSTGDEPKSCDKTHTCPPCP
APELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVMHE
ALHNHYTQKSLSLSPGKRPSGRKSSKMQAFRIWDVNQKTFYLRNNQLVAG
YLQGPNVNLKEKIDVVPIEPHALFLGIHGGKMCLSCVKSGDETRLQLEAV
NITDLSENRKQDKRFAFIRSDSGPTTSFESAACPGWFLCTAMEADQPVSL
TNMPDEGVMVTKFYFQEDE (2) Information for SEQ ID No:3: (Amino Acid Sequence of Mature TNFRII Extracellular Domain)
(i) Sequence characteristics: (A) Length: 235 amino acids; (B) Type: amino acid; (C) Topology: linear.
(ii) Molecular type: protein.
(iii) Sequence description: SEQ ID No:3: (amino acid sequence of mature TNFRII extracellular domain)

LPAQVAFTPYAPEPGSTCRLREYYDQTAQMCCSKCSPGQHAKVFCTKTSD
TVCDSCEDSTYTQLWNWVPECLSCGSRCSSDQVETQACTREQNRICTCRP
GWYCALSKQEGCRLCAPLRKCRPGFGVARPGTETSDVVCKPCAPGTFSNT
TSSTDICRPHQICNVVAIPGNASMDAVCTSTSPTRSMAPGAVHLPQPVST
RSQHTQPTPEPSTAPSTSFLLPMGPSPPAEGSTGD (2) Information for SEQ ID No:4: (Amino Acid Sequence of Human Immunoglobulin Fc Fragment)
(i) Sequence characteristics: (A) Length: 231 amino acids; (B) Type: amino acid; (C) Topology: linear.
(ii) Molecular type: protein.
(iii) Sequence description: SEQ ID No:4: (amino acid sequence of human immunoglobulin Fc fragment)

EPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKS
RWQQGNVFSCSVMHEALHNHYTQKSLSLSPG (2) Information for SEQ ID No:5: (Amino Acid Sequence of Mature IL-1ra)
(i) Sequence characteristics: (A) Length: 152 amino acids; (B) Type: amino acid; (C) Topology: linear.
(ii) Molecular type: protein.
(iii) Sequence description: SEQ ID No:5: (amino acid sequence of mature IL-1ra)

RPSGRKSSKMQAFRIWDVNQKTFYLRNNQLVAGYLQGPNVNLKEKIDVVP
IEPHALFLGIHGGKMCLSCVKSGDETRLQLEAVNITDLSENRKQDKRFAF
IRSDSGPTTSFESAACPGWFLCTAMEADQPVSLTNMPDEGVMVTKFYFQE
DE (2) Information for SEQ ID No:6:
(i) Sequence characteristics: (A) Length: 1467 bp; (B) Type: nucleic acid; (C) Strandedness: single; (D) Topology: linear.
(ii) Molecular Type: cDNA
(iii) Anti-sense: no.
(iv) Original source: homo sapiens.
(v) immediate source: synthetic.
(vi) Feature: full length coding sequence.
(vii) Feature: signal peptide 1-66.
(viii) Sequence description: SEQ ID No:6: (full length nucleotide coding sequence of TNFRII-Fc without stop codon)

atggcgcccgtcgccgtctgggccgcgctggccgtcggactggagctctgggctgcggcgcacgccttgcccgcccag
gtggcatttacaccctacgccccggagcccgggagcacatgccggctcagagaatactatgaccagacagctcagatgtg
ctgcagcaaatgctcgccgggccaacatgcaaaagtcttctgtaccaagacctcggacaccgtgtgtgactcctgtgagga
cagcacatacacccagctctggaactgggttcccgagtgcttgagctgtggctcccgctgtagctctgaccaggtggaaac
tcaagcctgcactcgggaacagaaccgcatctgcacctgcaggcccggctggtactgcgcgctgagcaagcaggaggg
gtgccggctgtgcgcgccgctgcgcaagtgccgcccgggcttcggcgtggccagaccaggaactgaaacatcagacgt
ggtgtgcaagccctgtgccccggggacgttctccaacacgacttcatccacggatatttgcaggcccaccagatctgtaa
cgtggtggccatccctgggaatgcaagcatggatgcagtctgcacgtccacgtccccaccggagtatggccccaggg
gcagtacacttacccccagccagtgtccacacgatcccaacacacgcagccaactccagaacccagcactgctccaagca
cctccttcctgctcccaatgggcccagccccagctgaagggagcactggcgacgagcccaaatcttgtgacaaaact
cacacatgcccaccgtgcccagcacctgaactcctgggggaccgtcagtcttcctcttccccccaaaacccaaggacac -continued

```
cctcatgatctcccggacccctgaggtcacatgcgtggtggtggacgtgagccacgaagaccctgaggtcaagttcaact ggtacgtggacggcgtggaggtgcataatgccaagacaaagccgcgggaggagcagtacaacagcacgtaccgtgtg gtcagcgtcctcaccgtcctgcaccaggactggctgaatggcaaggagtacaagtgcaaggtctccaacaaagccctccc agcccccatcgagaaaaccatctccaaagccaaagggcagccccgagaaccacaggtgtacaccctgcccccatcccg ggatgagctgaccaagaaccaggtcagcctgacctgcctggtcaaaggcttctatcccagcgacatcgccgtggagtggg agagcaatgggcagccggagaacaactacaagaccacgcctcccgtgctggactccgacggctccttcttcctctacagc aagctcaccgtggacaagagcaggtggcagcaggggaacgtcttctcatgctccgtgatgcatgaggctctgcacaacca ctacacgcagaagagcctctccctgtctccgggtaaa
```

(2) Information for SEQ ID No:7:
 (i) Sequence characteristics: (A) Length: 467 amino acids; (B) Type: amino acid; (C) Topology: linear.
 (ii) Molecular type: protein.
 (iii) Sequence description: SEQ ID No:7: (translated mature amino acid sequence of TNFRII-Fc)

```
LPAQVAFTPYAPEPGSTCRLREYYDQTAQMCCSKCSPGQHAKVFCTKTSD

TVCDSCEDSTYTQLWNWVPECLSCGSRCSSDQVETQACTREQNRICTCRP

GWYCALSKQEGCRLCAPLRKCRPGFGVARPGTETSDVVCKPCAPGTFSNT

TSSTDICRPHQICNVVAIPGNASMDAVCTSTSPTRSMAPGAVHLPQPVST

RSQHTQPTPEPSTAPSTSFLLPMGPSPPAEGSTGDEPKSCDKTHTCPPCP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHE

ALHNHYTQKSLSLSPGK
```

Example 2

Scale Up and Purification of TNFRII-Fc-IL-1ra and Control TNFRII-Fc

Cell lines were serum-free suspension adapted in CHO-CD4 medium (Irvine Scientific) and in-house feed medium, and scaled up in 3 liter bioreactor (Eplikon) and roller bottles. Both TNFRII-Fc-IL-1ra (SEQ ID No: 2) and control TNFRII-Fc (SEQ ID No: 7) could be produced at commercial level (at least 180 mg/L in 3 liter bioreactor). These proteins were purified by protein-A direct capture, followed by ion-exchange and hydrophobic chromatography (FIGS. 2, 3). Bulk purified proteins were formulated, lyophilized and SEC-HPLC analyzed (FIG. 4).

Example 3

The lyophilized proteins were subsequently used for TNF alpha binding and IL-1 receptor binding assays.

For IL-1 receptor binding assay, recombinant human IL-1 receptor extracellular domain was first produced in house using a mammalian host. TNFRII-Fc-IL-1ra, negative control TNFRII-Fc and positive control IL-1ra (KINERET) have been coated to 96-well plate. IL-1 receptor is then incubated at 37° C. for binding. The binding is detected using rabbit anti human IL-1 receptor extracellular domain antibodies, followed by goat anti rabbit IgO conjugated with HRP. FIG. 5 shows that both TNFRII-Fc-IL-1ra and IL-1ra (KINERET) bind to IL-1 receptor, and that TNFRII-Fc (ENBREL) does not bind.

For TNF alpha binding assay, recombinant TNF alpha has been coated on a 96 well plate. TNFRII-Fc-IL-1ra, positive control TNFRII-Fc (ENBREL) and negative control Tie2 (ANG-I receptor extracellular domain)-Fc was then incubated at 37° C. for binding. The binding was detected by anti human IgG Fc antibodies conjugated with HRP. FIGS. 6 and 7 show that both TNFRII-Fc-IL-1ra chimera and TNFRII-Fc bind to TNF alpha, and that negative control Tie2-Fc does not bind to TNF alpha.

Example 4

Bioassay and Functional Testing of TNFRII-Fc-IL-1ra, Control TNFRII-Fc (ENBREL), and Control IL-1ra (KINERET)

For cell-based IL-1 neutralization assay, IL-1 dependent D10 cells (ATCC) have been employed to test the blocking activity of IL-1ra (KINERET) and TNFRII-Fc-IL-1ra chimera against recombinant human IL-1's proliferation stimulating activity to D10 cells.

For cell-based TNF neutralization assay, L929 cells (ATCC) were employed to test TNFRII's blocking activity against TNF alpha (Biosource International).

Results of cell-based assays are shown in FIGS. 8-9. Taken together, functional TNFRII-Fc-IL-1ra chimera has been produced successfully. It maintains both TNF alpha and IL-1 neutralizing activity. Due to its mammalian produced nature with glycosylation and large size of the fused molecule, it has longer biological life than TNFRII-Fc (ENBREL).

Example 5

125-I Labeling and Animal Testing of TNFRII-Fc-IL-1ra Chimera and Control TNFRII-Fc 125-I labeled TNFRII-Fc-IL-1ra was made by using Iodogen method and purified by size-exclusion chromatography (M Hui et al., 1989). IL-1 receptor binding assay had been established by using in-house mammalian recombinant IL-receptor extracellular domain fused (see Example 3). IL-1 receptor binding to 125-I labeled TNFRI-Fc-IL-1ra was compared side by side with non-radiolabelled TNFRII-Fc (ENBREL), and negative control TNFRII-Fc.

Our data indicate that 125-I labeled TNFRII-Fc-IL-1ra is functional in terms of IL-1 receptor binding (Table 2).

125-I labeled TNFRII-Fc-IL-1ra was injected into skin inflammation mice model (see below) together with 125-I labeled TNFRII-Fc (ENBREL). Surprisingly, our result indicated that it was distributed more at inflammatory site than that of TNFRII-Fc (Table 3). This most probably is due to its IL-1 receptor binding affinity. Meanwhile TNFRII-Fc was also distributed more at inflammation site with lesser degree than that of TNFRII-Fc-IL-1ra. This may be explained by its TNF alpha binding affinity and high concentration of TNF alpha at inflammation site.

Mice treated with 6 nmol TPA by ear painting in 200 ul acetone consistently develop skin inflammation in 2-3 days. TNFRII-Fc (5 ug and 10 ug) and TNFRII-Fc-IL-1ra (2.5 ug, 5 ug and 10 ug) were administered over the entire period of skin inflammation development. Eight mice each group were injected with TNFRII-Fc and TNFRII-Fc-IL-1ra chimera every day from day 0-3. Administration of TNFRII-Fc systemically (intra-peritoneally) was shown effective in suppressing the symptoms of skin inflammation in mice (Table 3). Surprisingly, TNFRII-Fc-IL-1ra chimera was shown more effective than TNFRII-Fc while significantly lower effective dose for TNFRII-Fc-IL-1ra was demonstrated than that of TNFRII-Fc (Table 4).

Animal tests have been used to evaluate the properties of TNFRII-Fc-IL-1ra chimera in collagen induced arthritis model. Mice previously immunized with porcine type II collagen (CII) in complete Freund adjuvant consistently develop collagen-induced arthritis (CIA). Approximately 14-17 days post-immunization, symptoms of clinical arthritis began to appear in the mice, with 90-100% of the mice displaying severe arthritis by day 28. Mice were injected intraperitoneally with TNFRII-Fc, TNFRII-Fc-IL-1ra and negative control Fc fragment to determine the effect, effective dose an defective dosing frequency on CIA. Mice were assessed for symptoms of arthritis at 12 weeks post-immunization.

TNFRII-Fc (5 ug and 10 ug) and TNFRII-Fc-IL-1ra (2.5 ug, 5 ug and 10 ug) were administered over the entire period of CIA development. Eight mice each group is injected with TNFRII-Fc and TNFRII-Fc-IL-1ra every other day as well as once every 4 days from days 0-35. Administration of TNFRII-Fc systemically (intraperitoneally) is shown effective in suppressing the symptoms of CIA in mice (Table 5). Surprisingly, TNFRII-Fc-IL-1ra was shown more effective than TNFRII-Fc and had significantly reduced effective dose and effective dosing frequency (Table 5).

TABLE 2

IL-1 receptor binding to 125-I labeled and non-labeled TNFRII-Fc-IL-1ra (n = 3).

| Name | Binding OD (X ± SD) |
|---|---|
| TNFRII-Fc-IL-1ra 125-I labeled | 1.5 ± 0.3 |
| TNFRII-Fc-IL-1ra | 1.5 ± 0.2 |
| TNFRII-Fc (ENBREL) | 0.4 ± 0.3 |

TABLE 3

Distribution of 125-I labeled TNFRII-Fc-IL-1ra and TNFRII-Fc (ENBREL) in inflamed and non-inflamed skin tissues 4 hours after injection. The distribution is expressed as % of injected dose per gram of tissue (n = 6).

| Treatment | Tissue | % of injected dose per gram tissue (n = 6) |
|---|---|---|
| TNFRII-Fc-IL-1ra 125-I | Inflamed skin | 3.8 ± 0.2 |
| TNFRII-Fc-IL-1ra 125-I | Normal skin | 1.5 ± 0.1 |
| TNFRII-Fc (ENBREL) 125-I | Inflamed skin | 2.8 ± 0.2 |
| TNFRII-Fc (ENBREL) 125-I | Normal skin | 1.4 ± 0.2 |

TABLE 4

Effect of systemically administration of TNFRII-Fc-IL-1ra, TNFRII-Fc (ENBREL), concurrent use of TNFRII-Fc and IL-1ra and negative control Fc fragment during inductive stage on skin inflammation. The skin inflammation is expressed as ear swelling thickness × 10−2 mm (X ± SD)/incidence (% onset of total animal# at day 3) (n = 10).

| | 5 ug | 10 ug | 20 ug |
|---|---|---|---|
| TNFRII-Fc-IL-1ra | 4 ± 0.3/100% | 3 ± 0.2/100% | 3 ± 0.2/90% |
| TNFRII-Fc (ENBREL) | 8 ± 0.2/100% | 8 ± 0.2/100% | 7 ± 0.2/100% |
| TNFRII-Fc + IL-1ra | 8 ± 0.2/100% | 7 ± 0.2/100% | 7 ± 0.2/100% |
| Fc fragment control | 16 ± 0.2/100% | 15 ± 0.2/100% | 16 ± 0.3/100% |

TABLE 5

Effect of systemically administration of TNFRII-Fc-IL-1ra, TNFRII-Fc (ENBREL), concurrent use of TNFRII-Fc and IL-1ra and negative control Fc fragment during inductive stage on the onset of arthritis. The onset of arthritis is expressed as onset day (X ± SD)/incidence (% positive of total animal#) (n = 10).

| | 2.5 ug | 5 ug | 10 ug |
|---|---|---|---|
| TNFRII-Fc-IL-1ra | 27 ± 2/80% | 28 ± 2/70% | 32 ± 3/70% |
| TNFRII-Fc (ENBREL) | 24 ± 2/90% | 24 ± 2/100% | 24 ± 2/100% |
| TNFRII-Fc + IL-1ra | 24 ± 2/80% | 25 ± 2/90% | 25 ± 2/100% |
| Fc fragment control | 18 ± 2/100% | 19 ± 2/100% | 18 ± 3/100% |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

I claim:

1. A chimeric polypeptide comprising:
   (1) a TNF neutralizer domain;
   (2) an IL-1 receptor antagonist domain; and
   (3) a dimerization domain,
   wherein the three domains are operably linked and the chimeric polypeptide includes SEQ ID NO:2.

2. The chimeric polypeptide of claim 1, wherein the TNF neutralizer domain includes a domain that binds to mammalian TNF or IL-6.

3. The chimeric polypeptide of claim 2, wherein the TNF neutralizer domain includes an extracellular domain of mammalian TNF receptor (TNFR) or mammalian IL-6 receptor.

4. The chimeric polypeptide of claim 3, wherein the mammalian TNFR is TNFRII or TNFRII.

5. The chimeric polypeptide of claim 3, wherein the mammalian TNFR is human TNFRII.

6. The chimeric polypeptide of claim 1, wherein the IL-1 receptor antagonist domain includes an IL-1 receptor antagonist (IL-1ra).

7. The chimeric polypeptide of claim 6, wherein the IL-1ra is a glycosylated mammalian polypeptide.

8. The chimeric polypeptide of claim 1, wherein the dimerization domain includes a human Ig Fc fragment.

9. The chimeric polypeptide of claim 8, wherein the human Ig Fc fragment is an IgG1 Fc fragment.

10. The chimeric polypeptide of claim 1, wherein the chimeric polypeptide includes, from the N-terminus to the C-terminus, a TNF neutralizer domain, a dimerization domain, and an IL-1 receptor antagonist domain.

11. A polynucleotide comprising a sequence encoding the chimeric polypeptide of claim 1.

12. An isolated comprising a polynucleotide of claim 11.

13. The cell of claim 12, wherein the cell is a mammalian cell, a bacterial cell, a yeast cell, an insect cell, or a plant cell.

14. The cell of claim 13, wherein the cell is a CHO cell or a NSO cell or a SP/2/0 cell.

15. A composition comprising a chimeric polypeptide of claim 1 and a pharmaceutical acceptable carrier.

16. A composition comprising a polynucleotide of claim 11 and a pharmaceutical acceptable carrier.

17. A method of treating a TNF- and IL-1-dependent disorder, comprising administering to a subject in need thereof an effective amount of a composition of claim 15.

18. A vector comprising a polynucleotide of claim 11.

19. A method of producing a polypeptide, comprising culturing the cell of claim 12 in a medium under conditions permitting expression of a polypeptide encoded by the polynucleotide, and purifying the polypeptide from the cultured cell or the medium of the cell.

20. The method of claim 17, wherein the disorder is selected from the group consisting of an inflammatory disease, an acute hepatitis, a cardiovascular disease, a graft versus host disease, and a brain injury resulting from trauma, epilepsy, hemorrhage, or stroke.

21. The method of claim 20, wherein the disorder is an inflammatory disorder.

22. The method of claim 21, wherein the inflammatory disorder is rheumatoid arthritis or psoriasis.

23. The method of claim 20, wherein the disorder is a cardiovascular disease or a brain injury resulting from stroke.

* * * * *